(12) United States Patent
Kassab et al.

(10) Patent No.: US 11,065,319 B2
(45) Date of Patent: *Jul. 20, 2021

(54) METHODS FOR DIAGNOSING AND REDUCING INCIDENCES OF CARDIAC ALLOGRAFT REJECTION

(71) Applicant: 3DT Holdings, LLC, San Diego, CA (US)

(72) Inventors: Ghassan S. Kassab, La Jolla, CA (US); Carlos A. Labarrere, San Diego, CA (US)

(73) Assignee: 3DT Holdings, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/789,752

(22) Filed: Oct. 20, 2017

(65) Prior Publication Data

US 2018/0043015 A1 Feb. 15, 2018

Related U.S. Application Data

(63) Continuation-in-part of application No. 14/614,239, filed on Feb. 5, 2015, now Pat. No. 10,500,260.

(60) Provisional application No. 62/412,912, filed on Oct. 26, 2016, provisional application No. 62/410,554, filed on Oct. 20, 2016, provisional application No. 62/042,562, filed on Aug. 27, 2014, provisional application No. 61/935,525, filed on Feb. 4, 2014.

(51) Int. Cl.

| | |
|---|---|
| *G01N 33/68* | (2006.01) |
| *G01N 33/86* | (2006.01) |
| *A61K 39/00* | (2006.01) |
| *A61K 31/14* | (2006.01) |
| *A61K 39/395* | (2006.01) |
| *C12N 5/0786* | (2010.01) |
| *A61K 35/12* | (2015.01) |
| *C07K 16/00* | (2006.01) |

(52) U.S. Cl.
CPC ........ *A61K 39/0013* (2013.01); *A61K 39/001* (2013.01); *G01N 33/68* (2013.01); *G01N 33/686* (2013.01); *G01N 33/6854* (2013.01); *G01N 33/86* (2013.01); *A61K 31/14* (2013.01); *A61K 39/0012* (2013.01); *A61K 39/39566* (2013.01); *A61K 2035/124* (2013.01); *C07K 16/00* (2013.01); *C12N 5/0645* (2013.01); *G01N 33/6893* (2013.01); *G01N 2333/4712* (2013.01); *G01N 2333/70525* (2013.01); *G01N 2333/745* (2013.01); *G01N 2333/968* (2013.01); *G01N 2800/245* (2013.01); *G01N 2800/50* (2013.01)

(58) Field of Classification Search
CPC ......... A61K 39/39566; A61K 39/0013; G01N 33/68; G01N 33/6854; G01N 33/86; G01N 33/686
See application file for complete search history.

(56) References Cited

U.S. PATENT DOCUMENTS

| | | | | |
|---|---|---|---|---|
| 2007/0286868 | A1* | 12/2007 | De Faire | C07K 16/18 424/179.1 |
| 2008/0118522 | A1* | 5/2008 | Lobo | C07K 16/06 424/172.1 |

OTHER PUBLICATIONS

Labarrere et al, 2000 (JAMA. 284: 457-464).*

* cited by examiner

*Primary Examiner* — Zachary C Howard
(74) *Attorney, Agent, or Firm* — Reichel Stohry Dean LLP; Mark C. Reichel; Natalie J. Dean

(57) ABSTRACT

Methods and products for diagnosing, treating and/or delaying onset of chronic allograft rejection, including cardiac allograft vasculopathy. In an exemplary embodiment of a noninvasive method of screening a cardiac allograft recipient for being at-risk for developing cardiac allograft vasculopathy of the present disclosure, the method comprises the steps of withdrawing at least one biological sample from a cardiac allograft recipient; and analyzing the at least one biological sample for one or more biomarkers indicative of the presence of fibrin deposits within the cardiac allograft microvasculature; wherein detection of the one or more biomarkers indicates that the cardiac allograft recipient is at-risk for or developing cardiac allograft vasculopathy.

18 Claims, 13 Drawing Sheets

METHODS FOR DIAGNOSING AND REDUCING INCIDENCES OF CARDIAC ALLOGRAFT REJECTION

RELATED APPLICATIONS

This application (I) is related to, and claims the priority benefit of, U.S. Provisional Patent Application Ser. No. 62/412,912, filed Oct. 26, 2016, (II) is related to, and claims the priority benefit of, U.S. Provisional Patent Application Ser. No. 62/410,554, filed Oct. 20, 2016, and (III) is related to, claims the priority benefit of, and is a U.S. continuation-in-part patent application of, U.S. Nonprovisional patent application Ser. No. 14/614,239 of Kassab et al., filed Feb. 4, 2015, which is related to, and claims the priority benefit of, U.S. Provisional Patent Application Ser. No. 61/935,525 of Kassab et al., filed Feb. 4, 2014; and (b) U.S. Provisional Patent Application Ser. No. 62/042,562 to Kassab of al., filed Aug. 27, 2014. The contents of each the aforementioned applications are hereby incorporated by reference in their entireties into this disclosure.

BACKGROUND

Graft rejection is the main obstacle to the long-term survival of any transplanted organ. To date, the primary strategy for curbing rejection has been to reduce the recipient's cellular and antibody-mediated capacity to attack donor cells in the transplanted organ. This strategy has encouraged researchers to develop immunosuppressive drugs designed to reduce the recipient's T-cell population (i.e. the instigators of cellular rejection), and to focus exclusively on therapeutic measures that subdue antibody-mediated rejection (AMR) of the transplanted organ. For over twenty years, modern immunosuppressive therapies have been used successfully to protect the allograft (i.e. transplanted organ/tissue) from acute cellular rejection, which has in turn bolstered the perception that the patient's immune system is harmful and that immune suppression is beneficial. However, although successful for acute graft rejection, this strategy has not reduced the incidence of chronic rejection and additionally serves to increase the likelihood of infection and malignancy long-term.

Specifically, despite some of the benefits of the above immunosuppressive strategy, it has been reported that high levels of immunoglobulin (Ig) M antibodies, a component of innate immunity, are in fact associated with a lower incidence of chronic allograft failure and longer patient survival. This implies that certain components of the recipient's innate immune system may actually be beneficial and should not be suppressed. Despite this, research focusing on the potential benefits of enhancing the recipient's immune response has not conventionally been pursued for several reasons. Primarily, the mechanism responsible for this potentially beneficial association has historically been unknown. Additionally, the prevailing dogma is currently that the recipient's immune system is harmful and should thus be suppressed to protect the foreign allograft from the host body's own defenses. As such, strategies that bolster the patient's immune system are in direct conflict with the dominant medical standards. Indeed, a recent consensus panel has even suggested reconsidering the term AMR, pursuant to theory that identifying donor-specific antibodies is no longer deemed necessary to establish the presence of allograft rejection. Without a proven antibody target, the decision to prevent or treat AMR lacks a mechanistic foundation and rests solely on clinical manifestations of graft failure that are observed in patients with biopsy specimens negative for cellular rejection. Accordingly, it is evident that the success of immunosuppression in combating the early effects of acute cellular rejection has largely lulled researchers into accepting a potentially false paradigm—that harmful immune-related mechanisms must also be involved in producing the late effects seen in chronic rejection. This paradigm has served as the primary motivation for a largely single-minded effort to discover the antibody-mediated source of chronic rejection.

Heart transplantation is the gold standard treatment for refractory advanced heart failure; however, allograft rejection continues to limit graft and patient survival. Despite the advances in immunosuppression and treatment of cardiac allograft rejection, which have improved one-year survival rates, in line with the above-described issues with immunosuppressive therapy, the late outcomes remain dismal with chronic rejection. Chronic cardiac allograft rejection is otherwise known as cardiac allograft vasculopathy (CAV), which is the major cause of long-term morbidity and mortality in cardiac allograft patients. Although CAV's etiology is unknown, several immunological and non-immunological causes have been proposed, including the involvement of innate immunity, inflammation, and coagulation. Innovative clinical and basic research is urgently needed to develop evidence-based therapies to prolong survival of cardiac transplant recipients. The elucidation of the mechanisms involved in late rejection is a critical step in identifying strategies and developing therapies to protect transplanted organs and improve clinical outcomes in patients.

CAV is the principal long-term cause of cardiac graft failure. Although modern immunosuppressive regimens have extended early survival by substantially reducing acute rejection, this has not impacted the incidence of CAV. The confirmed CAV-related deaths become prominent within 1 to 3 years post-transplant and continue to significantly contribute to mortality in subsequent years: 8% at 1 year, 20% at 3 years, 30% at 5 years, and more than 50% at 10 years. (Additionally, deaths from infection and malignancy, possible results of over-immunosuppression, are also prominent as the years progress post-transplant.) Although CAV is a risk factor for long-term mortality, the diagnosis of CAV has a short-term mortality risk (10% of patients die within 1 year of diagnosis). Remarkably, the long-term survival of patients alive one year after transplantation has not improved appreciably in the last 20 years.

Accordingly, there is a need to better understand the physiological and biological mechanisms involved in chronic rejection. Furthermore, a significant need exists for the identification of clinically useful early risk predictors to facilitate early identification of the onset of chronic allograft failure—e.g., to identify those patients most susceptible to developing long-term CAV and CAV-associated allograft failure—as well as to develop an effective strategy for preventing the chronic rejection (including CAV).

The development of new options for the early detection of patients at risk of CAV can prolong the survival of cardiac transplant recipients. Early identification of CAV became possible with the introduction of intravascular ultrasound (IVUS), an invasive technique usually not initiated until at least one year post-transplantation. IVUS is expensive, poses increased risks, and lacks the ability to assess the entire coronary tree. Other invasive tests (e.g., using endomyocardial biopsies) and less invasive tests like stress perfusion, dobutamine echocardiography, ultrafast tomography, and MRI are not sufficiently sensitive or specific to detect early stages of the disease. In view of the same, there is a need to develop a novel diagnostic tool for identifying at-risk patients by detecting early depletion of natural antibodies (NAbs) to phosphorylcholine (PC—one of the key epitopes found on oxLDL, but not native LDL) and creating an evidential base for the pursuit of early vaccine therapies to prevent or ameliorate disease progression. This is particularly relevant given that 10-20% recipients have angiographic evidence of CAV in the first year post-transplantation. CAV increases 10% per year and at 5 years, 50% of patients have some evidence of CAV, which is one of the leading causes of death with a 2-year survival rate of <15% in those with extended disease.

In view of the foregoing, a determination of the protective role that innate immunity plays in CAV would be well received by the scientific and medical communities, as said determinations may lead to diagnostic tools to identify and lead to treatment of at-risk patients.

BRIEF SUMMARY

In at least one exemplary embodiment of the present disclosure, a method of screening an allograft recipient for chronic rejection or being at-risk for developing the same is disclosed. Embodiments of such method comprise the steps of: measuring an amount of a first natural antibody within at least one biological sample from an allograft recipient; and comparing the amount of the first natural antibody in the biological sample with the amount of the first natural antibody in a control sample; wherein a decrease in the amount of the first natural antibody in the sample from the allograft recipient as compared to the amount of the first natural antibody in the control sample indicates a diagnosis of the allograft recipient being either at-risk for or experiencing chronic allograft rejection. In at least one embodiment, the allograft comprises a cardiac allograft and the chronic allograft rejection comprises cardiac allograft vasculopathy.

In certain embodiments, the first natural antibody of the method may be selected from the group consisting of immunoglobulin M, immunoglobulin G, and immunoglobulin A, and the at least one biological sample comprises tissue. In such embodiments, the step of comparing the amount of the first natural antibody in the biological sample with the amount of the first natural antibody in a control sample may comprise reacting the at least one biological sample with Arginase I and analyzing the degree of reactivity within the sample; wherein the degree of reactivity in the at least one biological sample is indicative of immunoglobulin M anti-phosphorylcholine, immunoglobulin G anti-phosphorylcholine, or immunoglobulin A anti-phosphorylcholine levels in the allograft recipient's serum. Additionally or alternatively, the method may further comprise the step of associating the patient with an increased risk of developing chronic allograft rejection when the amount of the first natural antibody is less than about 20 units/ml of serum.

In yet other embodiments, the first natural antibody comprises either immunoglobulin M anti-phosphorylcholine, immunoglobulin G anti-phosphorylcholine, or immunoglobulin A anti-phosphorylcholine, and at least one of the biological samples comprises serum.

Additional embodiments of the method further comprise the step of withdrawing at least one biological sample from the allograft recipient. In at least one embodiment, the at least one biological sample comprises serum or tissue. Additionally or alternatively, if the diagnosis of the allograft recipient is indicated as being at-risk for or experiencing chronic allograft rejection, the method may further comprise the step of selectively enhancing a natural antibody-mediated innate immune response in the allograft recipient. Optionally, the step of selectively enhancing a natural antibody-mediated immune response may further comprise increasing levels of immunoglobulin M and/or immunoglobulin G anti-phosphorylcholine natural antibodies in the allograft recipient's serum.

Particular embodiments of the method of the present disclosure further comprise the step of administering a vaccine to the allograft recipient. Perhaps more specifically, in at least one embodiment, the step of increasing levels of immunoglobulin M and/or immunoglobulin G anti-phosphorylcholine natural antibodies in the allograft recipient's serum further comprises administering a vaccine to the allograft recipient, the vaccine comprising a composition for preventing or treating chronic allograft rejection, wherein the composition comprises a therapeutically effective amount of phosphorylcholine sufficient to initiate the production of anti-phosphorylcholine natural antibodies in a mammal following administration thereto. In at least some embodiments, the vaccine is administered before chronic allograft rejection is detected.

In at least one exemplary embodiment of the screening method of the present disclosure, the increased levels of immunoglobulin M and/or immunoglobulin G anti-phosphorylcholine natural antibodies in the allograft recipient's serum induces alternative M2 anti-inflammatory macrophage polarization. Additionally or alternatively, the method may further comprise the step of clearing the allograft of damaged cells by way of inducing alternative M2 anti-inflammatory macrophage polarization. In yet other embodiments, the step of selectively enhancing a natural antibody-mediated immune response may result in the reduction or prevention of atherosclerosis in the allograft.

The present disclosure also provides for additional exemplary embodiments of a noninvasive method of screening a cardiac allograft recipient for being at-risk for developing cardiac allograft vasculopathy. In such embodiments, the method comprises the steps of: withdrawing at least one biological sample from a cardiac allograft recipient; and analyzing the at least one biological sample for one or more biomarkers indicative of the presence of fibrin deposits within the cardiac allograft microvasculature; wherein detection of the one or more biomarkers indicates that the cardiac allograft recipient is at-risk for or developing cardiac allograft vasculopathy. The step of withdrawing the at least one biological sample may comprise withdrawing serum from the cardiac allograft recipient. Furthermore, in at least one exemplary embodiment, at least one of the biomarkers is selected from the group comprising: an elevated level of cardiac troponin I in the serum as compared to a control serum sample, and detection of reduced anticoagulant and fibrinolytic capacities of the serum as compared to a control serum sample.

Additionally or alternatively, the step of withdrawing the at least one biological sample may comprise extracting a biopsy sample of the cardiac allograft, the biopsy sample comprising endothelial cells; and at least one of the biomarkers is selected from the group comprising: detection of up-regulation of endothelial intercellular adhesion molecule-1 (ICAM-1) expression in endothelial cells from the biopsy sample as compared to a control tissue sample, and detection of an elevated nuclear factor-kappa B (NF-κB) nuclear expression in the endothelial cells from the biopsy sample as compared to a control tissue sample. In still another embodiment, if the cardiac allograft recipient is diagnosed as being at-risk or developing cardiac allograft vasculopathy, the method further comprises the step of: selectively enhancing a natural antibody-mediated innate immune response in the allograft recipient by administering a vaccine to the allograft recipient; wherein the vaccine comprises a composition for preventing or treating chronic allograft rejection, the composition comprising a therapeutically effective amount of phosphorylcholine sufficient to initiate the production of anti-phosphorylcholine natural antibodies in a mammal following administration thereto.

Still further, other noninvasive methods of diagnosing the early onset of chronic allograft rejection are provided. In at least one exemplary embodiment, such a method comprises the steps of: measuring an amount of a first natural antibody within at least one biological sample from a cardiac allograft recipient; comparing the amount of the first natural antibody in the biological sample with the amount of the first natural antibody in a control sample; analyzing the at least one biological sample for one or more biomarkers indicative of the presence of fibrin deposits within the cardiac allograft microvasculature; wherein a decrease in the amount of the first natural antibody in the sample from the cardiac allograft recipient as compared to the amount of the first natural antibody in the control sample indicates a diagnosis of the allograft recipient being either at-risk for or developing chronic allograft rejection; and wherein detection of the one or more biomarkers in the at least one biological sample indicates that the cardiac allograft recipient is at-risk for or developing cardiac allograft vasculopathy.

In an exemplary embodiment of a composition for preventing or treating chronic allograft rejection, the composition comprises a therapeutically effective amount of phosphorylcholine sufficient to initiate the production of anti-phosphorylcholine natural antibodies in a mammal following administration thereto. In an additional embodiment, the phosphorylcholine comprises phosphorylcholine hapten conjugated to keyhold limpet hemocyanin. Furthermore, other embodiments comprise a composition for preventing or treating chronic allograft rejection, such compositions comprising a therapeutically effective amount of natural antibodies sufficient to induce alternative M2 anti-inflammatory macrophage polarization in a mammal following administration thereto.

In at least one embodiment of an exemplary method for preventing or treating allograft rejection in an allograft recipient, the method comprises the step of selectively enhancing a natural antibody-mediated immune response in the allograft recipient. In at least one embodiment, the step of enhancing a natural antibody-mediated immune response results in reducing or preventing fibrosis in the allograft and/or the allograft comprises a cardiac allograft. In at least one alternative embodiment, the step of selectively enhancing a natural antibody-mediated immune response may further comprise increasing levels of immunoglobulin M and/or immunoglobulin G anti-phosphorylcholine natural antibodies in the allograft recipient's serum. Additionally, the increased levels of immunoglobulin M and/or immunoglobulin G anti-phosphorylcholine natural antibodies in the allograft recipient's serum may induce alternative M2 anti-inflammatory macrophage polarization. Still further, in at least one embodiment, the method further comprises the step of clearing the allograft of damaged cells by way of inducing alternative M2 anti-inflammatory macrophage polarization.

Additionally or alternatively, the step of increasing levels of immunoglobulin M and/or immunoglobulin G anti-phosphorylcholine natural antibodies in the allograft recipient's serum may further comprise administering a vaccine to the allograft recipient, the vaccine comprising the previously described composition. In yet another embodiment, the method may comprise the step of administering the vaccine before chronic allograft rejection is detected. In certain embodiments of the methods of the present disclosure, the allograft may comprise a cardiac allograft and the step of selectively enhancing a natural antibody-mediated immune response may comprise increasing levels of myocardial immunoglobulin M and/or immunoglobulin G natural antibodies in the microvasculature of the cardiac allograft.

An additional exemplary embodiment of the present disclosure comprises a method of screening an allograft recipient for chronic allograft rejection or being at-risk for developing the same. Embodiments of such method comprise the steps of: measuring an amount of a first natural antibody within at least one biological sample from a patient; and comparing the amount of the first natural antibody in the biological sample with the amount of the first natural antibody in a control sample; wherein a decrease in the amount of the first natural antibody in the sample from the allograft recipient as compared to the amount of the first natural antibody in the control sample indicates a diagnosis of the allograft recipient being either at-risk for or experiencing chronic allograft rejection. In at least one alternative, albeit perhaps similar, embodiment, the method may comprise the steps of: measuring an amount of a first natural antibody within at least one biological sample from a patient; and associating the patient with an increased risk of developing chronic allograft rejection when the amount of the first natural antibody is less than 20 units/ml. Embodiments of the aforementioned methods may additionally comprise the step of withdrawing at least one biological sample from an allograft recipient. Further, the allograft of such methods may comprise a cardiac allograft and, in such case, the chronic allograft rejection may comprise cardiac allograft vasculopathy.

The first natural antibody in the at least one biological sample may be selected from the (nonexclusive) group consisting of immunoglobulin M and immunoglobulin G. Furthermore, in at least one embodiment, the at least one biological sample comprises serum or tissue. When at least one of the biological samples comprises serum, in at least one embodiment, the first natural antibody may comprise immunoglobulin M anti-phosphorylcholine.

In yet another embodiment of the present disclosure, a method of screening a cardiac allograft recipient for being at-risk for developing cardiac allograft vasculopathy is disclosed. Embodiments of such method comprise the steps of: withdrawing a first biological sample from a cardiac allograft of the cardiac allograft recipient; and detecting elevated cardiac troponin I levels in the first biological sample; wherein elevated levels of cardiac troponin I as compared to those of a control sample indicates a diagnosis of the cardiac allograft recipient being at-risk for developing cardiac allograft vasculopathy. Additional embodiments further comprise the steps of: withdrawing a second biological sample from serum of the cardiac allograft recipient; detecting a lack of anticoagulant and fibrinolytic capacity and up-regulation of endothelial intercellular adhesion molecule-1 (ICAM-1) in the serum; and diagnosing the cardiac allograft recipient as being at-risk for developing cardiac allograft vasculopathy.

In an exemplary embodiment of a method for reducing an incidence of transplant rejection of the present disclosure, the method comprises the step of treating an individual who has or will receive transplanted tissue with at least one substance sufficient to increase innate immunity of the individual. In various embodiments, the transplanted tissue comprises heart tissue or tissue of any other solid organ transplant, including, but not limited to, kidney, lung, liver, intestines, and pancreas. In several embodiments, the transplanted tissue comprises a heart or any other solid organ. In a number of embodiments, the treatment step is performed to reduce an incidence of cardiac allograft vasculopathy (CAV, atherosclerosis in a transplanted organ) or chronic rejection in other solid organs. In numerous embodiments, the treatment step is performed to reduce the risk of CAV or any other chronic rejection of a transplanted solid organ.

In an exemplary embodiment of a method for reducing an incidence of transplant rejection of the present disclosure, the treatment step is performed to prevent chronic rejection. In numerous embodiments, the treatment step is performed to increase a B-cell population within the individual. In various embodiments, the treatment step is performed to enhance B-cell activity within the individual. In several embodiments, the treatment step is performed to increase a level of immunoglobulin (Ig) M antibodies within the individual. In a number of embodiments, the treatment step is performed to enhance immunoglobulin (Ig) M antibody activity within the individual.

In an exemplary embodiment of a method for reducing an incidence of transplant rejection of the present disclosure, the Ig-M antibody or antibodies is/are Ig-M anti-phosphorylcholine (PC) antibodies. In a number of embodiments, the treatment step is performed to decrease activity of C-reactive protein within the individual. In numerous embodiments, the treatment step is performed to suppress C-reactive protein activity within the individual. In various embodiments, the treatment step is performed so to polarize classically activated macrophages toward alternatively activated macrophages within the individual. In several embodiments, the treatment step is performed so to increase a population of alternatively activated macrophages within the individual.

In an exemplary embodiment of a method for reducing an incidence of transplant rejection of the present disclosure, the treatment step is performed so to decrease a population of classically activated macrophages within the individual. In several embodiments, the treatment step is performed to reduce an incidence of foam cell formation caused by classically activated macrophages. In a number of embodiments, the treatment step is performed to prevent foam cell formation caused by classically activated macrophages. In numerous embodiments, the treatment step is performed to cause a population of macrophages within the individual to release anti-inflammatory cytokines to promote macrophage clearance. In various embodiments, the treatment step is performed to reduce accumulation of macrophages within a vessel wall of the transplanted tissue.

In an exemplary embodiment of a method for reducing an incidence of transplant rejection of the present disclosure, the at least one substance comprises a vaccine. In various embodiments, the at least one substance comprises phosphorylcholine. In several embodiments, the at least one substance comprises Ig-M anti-PC. In a number of embodiments, the at least one substance stimulates production of Ig-M anti-PC within the individual. In numerous embodiments, the at least one substance causes a reduction of an incidence of inflammation within the individual.

In an exemplary embodiment of a method for reducing an incidence of transplant rejection of the present disclosure, the at least one substance causes a reduction of a size of a lesion within the transplanted tissue within the individual. In numerous embodiments, the treatment step is performed to reduce an incidence of acute or chronic rejection of the transplanted tissue. In various embodiments, the treatment step is performed to reduce the risk of acute or chronic rejection of the transplanted tissue. In several embodiments, the treatment step is performed to prevent acute or chronic rejection of the transplanted tissue. In a number of embodiments, the individual has received the transplanted tissue, and wherein the individual has expressed at least one symptom of transplant rejection.

In an exemplary embodiment of a method for reducing an incidence of transplant rejection of the present disclosure, the at least one symptom of transplant rejection comprises at least one symptom of acute transplant rejection. In a number of embodiments, the at least one symptom of transplant rejection comprises at least one symptom of chronic transplant rejection. In numerous embodiments, the individual exhibits at least one marker associated with the markers selected from the group consisting of endothelial activation, coagulation, and chronic inflammation. In various embodiments, the treatment step is performed to enhance interleukin-10 (IL-10) production within the individual. In several embodiments, the treatment step is performed to increase a concentration of IL-10 within the individual.

In an exemplary embodiment of a method for reducing an incidence of transplant rejection of the present disclosure, the treatment step is performed to stimulate alternatively activated macrophages within the individual to increase production of IL-10 within the individual. In several embodiments, the treatment step is performed to enhance transforming growth factor-beta (TGF-$\beta$) production within the individual. In a number of embodiments, the treatment step is performed to increase a concentration of TGF-$\beta$ within the individual. In numerous embodiments, the treatment step is performed to stimulate alternatively activated macrophages within the individual to increase production of TGF-$\beta$ within the individual. In various embodiments, the treatment step is performed to enhance arginase-1 production within the individual.

In an exemplary embodiment of a method for reducing an incidence of transplant rejection of the present disclosure, the treatment step is performed to increase a concentration of arginase-1 within the individual. In various embodiments, the treatment step is performed to stimulate alternatively activated macrophages within the individual to increase production of arginase-1 within the individual.

In an exemplary embodiment of a method for reducing an incidence of transplant rejection of the present disclosure, the method comprises the step treating an individual who has received transplanted tissue and who has experienced at least one symptom of transplant rejection with at least one substance sufficient to increase innate immunity of the individual. In several embodiments, the at least one substance comprises PC. In various embodiments, the at least one substance comprises Ig-M anti-PC.

In an exemplary embodiment of a substance for reducing an incidence of transplant rejection of the present disclosure, the substance comprises PC. In an exemplary embodiment of a substance for reducing an incidence of transplant rejection of the present disclosure, the substance comprises Ig-M anti-PC. In an exemplary embodiment of a vaccine for reducing an incidence of transplant rejection of the present disclosure, the vaccine comprises PC. In an exemplary embodiment of a vaccine for reducing an incidence of transplant rejection of the present disclosure, the vaccine comprises Ig-M anti-PC.

In an exemplary embodiment of a method and/or use of a substance and/or vaccine of the present disclosure, the method is performed, and/or the substance and/or vaccine is/are used, to treat an individual having atherosclerosis. In various embodiments, the individual is diabetic, hypertensive, hyperlipidemic, a smoker (current or former), and/or has experienced pre-eclampsia.

In an exemplary embodiment of a noninvasive method of screening a cardiac allograft recipient for being at-risk for developing cardiac allograft vasculopathy of the present disclosure, the method comprises the steps of withdrawing at least one biological sample from a cardiac allograft recipient; and analyzing the at least one biological sample for one or more biomarkers indicative of the presence of fibrin deposits within the cardiac allograft microvasculature; wherein detection of the one or more biomarkers indicates that the cardiac allograft recipient is at-risk for or developing cardiac allograft vasculopathy.

In an exemplary embodiment of a noninvasive method of screening a cardiac allograft recipient for being at-risk for developing cardiac allograft vasculopathy of the present disclosure the step of withdrawing the at least one biological sample comprises withdrawing serum from the cardiac allograft recipient; and at least one of the biomarkers is selected from the group comprising an elevated level of cardiac troponin I in the serum as compared to a control serum sample, and detection of reduced anticoagulant and fibrinolytic capacities of the serum as compared to a control serum sample.

In an exemplary embodiment of a noninvasive method of screening a cardiac allograft recipient for being at-risk for developing cardiac allograft vasculopathy of the present disclosure, the step of withdrawing the at least one biological sample comprises extracting a biopsy sample from the cardiac allograft recipient, the biopsy sample comprising endothelial cells; and at least one of the biomarkers is selected from the group comprising detection of up-regulation of endothelial intercellular adhesion molecule-1 (ICAM-1) expression in endothelial cells from the biopsy sample as compared to a control tissue sample, and detection of an elevated nuclear factor-kappa B (NF-κB) nuclear expression in the endothelial cells from the biopsy sample as compared to a control tissue sample.

In an exemplary embodiment of a noninvasive method of screening a cardiac allograft recipient for being at-risk for developing cardiac allograft vasculopathy of the present disclosure, if the cardiac allograft recipient is at-risk of developing cardiac allograft vasculopathy, the method further comprises the step of selectively enhancing a natural antibody-mediated innate immune response in the allograft recipient by increasing levels of immunoglobulin M and/or immunoglobulin G anti-phosphorylcholine natural antibodies in an allograft recipient's serum.

In an exemplary embodiment of a noninvasive method of screening a cardiac allograft recipient for being at-risk for developing cardiac allograft vasculopathy of the present disclosure, the step of increasing levels of immunoglobulin M and/or immunoglobulin G anti-phosphorylcholine natural antibodies in an allograft recipient's serum further comprises administering a vaccine to the allograft recipient, the vaccine comprising a composition for preventing or treating chronic allograft rejection; and the composition further comprising a therapeutically effective amount of phosphorylcholine sufficient to initiate the production of anti-phosphorylcholine natural antibodies in a mammal following administration thereto.

In an exemplary embodiment of a noninvasive method of screening a cardiac allograft recipient for being at-risk for developing cardiac allograft vasculopathy of the present disclosure, the vaccine is administered before chronic allograft rejection is detected.

In an exemplary embodiment of a noninvasive method of screening a cardiac allograft recipient for being at-risk for developing cardiac allograft vasculopathy of the present disclosure, the step of selectively enhancing a natural antibody-mediated immune response results in the reduction or prevention of atherosclerosis in the allograft recipient.

In an exemplary embodiment of a noninvasive method of screening a cardiac allograft recipient for being at-risk for developing cardiac allograft vasculopathy of the present disclosure, the step of selectively enhancing a natural antibody-mediated immune response results in the reduction of risk factors in Cardiac Allograft Vasculopathy (CAV), Major Cardiac Events (MACE), and Graft Failure Due to CAV (GFDCAV).

In an exemplary embodiment of a noninvasive method of screening a cardiac allograft recipient for being at-risk for developing cardiac allograft vasculopathy of the present disclosure, the increased levels of immunoglobulin M and/or immunoglobulin G anti-phosphorylcholine natural antibodies in the allograft recipient's serum induces alternative M2 anti-inflammatory macrophage polarization.

In an exemplary embodiment of a noninvasive method of screening a cardiac allograft recipient for being at-risk for developing cardiac allograft vasculopathy of the present disclosure, the method further comprises the step of clearing the allograft of damaged cells by way of inducing alternative M2 anti-inflammatory macrophage polarization.

In an exemplary embodiment of a noninvasive method of diagnosing early onset of chronic allograft rejection of the present disclosure, the method comprises the steps of measuring an amount of a first natural antibody within at least one biological sample from a cardiac allograft recipient; comparing the amount of the first natural antibody in the biological sample with the amount of the first natural antibody in a control sample; analyzing the at least one biological sample for one or more biomarkers indicative of the presence of fibrin deposits within the cardiac allograft microvasculature; wherein a decrease in the amount of the first natural antibody in the sample from the cardiac allograft recipient as compared to the amount of the first natural antibody in the control sample indicates a diagnosis of the allograft recipient being either at-risk for or developing chronic allograft rejection; and wherein detection of the one or more biomarkers in the at least one biological sample indicates that the cardiac allograft recipient is at-risk for or developing cardiac allograft vasculopathy.

In an exemplary embodiment of a noninvasive method of diagnosing early onset of chronic allograft rejection of the present disclosure, the method further comprises the step of withdrawing the at least one biological sample by withdrawing serum from the cardiac allograft recipient; and wherein at least one of the biomarkers is selected from the group comprising an elevated level of cardiac troponin I in the serum as compared to a control serum sample, and detection of reduced anticoagulant and fibrinolytic capacities of the serum as compared to a control serum sample.

In an exemplary embodiment of a noninvasive method of diagnosing early onset of chronic allograft rejection of the present disclosure, the method further comprises the step of withdrawing the at least one biological sample, wherein withdrawing the at least one biological sample comprises extracting a biopsy sample from the cardiac allograft recipient, the biopsy sample comprising endothelial cells; and at least one of the biomarkers is selected from the group comprising detection of up-regulation of endothelial intercellular adhesion molecule-1 (ICAM-1) expression in endothelial cells from the biopsy sample as compared to a control tissue sample, and detection of an elevated nuclear factor-kappa B (NF-κB) nuclear expression in the endothelial cells from the biopsy sample as compared to a control tissue sample.

In an exemplary embodiment of a noninvasive method of diagnosing early onset of chronic allograft rejection of the present disclosure, the method further comprises the step of selectively enhancing a natural antibody-mediated innate immune response in the allograft recipient by increasing levels of immunoglobulin M and/or immunoglobulin G anti-phosphorylcholine natural antibodies in an allograft recipient's serum.

In an exemplary embodiment of a noninvasive method of diagnosing early onset of chronic allograft rejection of the present disclosure, the step of increasing levels of immunoglobulin M and/or immunoglobulin G anti-phosphorylcholine natural antibodies in an allograft recipient's serum further comprises administering a vaccine to the allograft recipient, the vaccine comprising a composition for preventing or treating chronic allograft rejection; and the composition further comprising a therapeutically effective amount of phosphorylcholine sufficient to initiate the production of anti-phosphorylcholine natural antibodies in a mammal following administration thereto.

In an exemplary embodiment of a noninvasive method of diagnosing early onset of chronic allograft rejection of the present disclosure, the step of selectively enhancing a natural antibody-mediated immune response results in the reduction or prevention of atherosclerosis in the allograft recipient.

In an exemplary embodiment of a noninvasive method of diagnosing early onset of chronic allograft rejection of the present disclosure, the step of selectively enhancing a natural antibody-mediated immune response results in the reduction of risk factors in Cardiac Allograft Vasculopathy (CAV), Major Cardiac Events (MACE), and Graft Failure Due to CAV (GFDCAV).

In an exemplary embodiment of a noninvasive method of diagnosing early onset of chronic allograft rejection of the present disclosure, the increased levels of immunoglobulin M and/or immunoglobulin G anti-phosphorylcholine natural antibodies in the allograft recipient's serum induces alternative M2 anti-inflammatory macrophage polarization.

In an exemplary embodiment of a noninvasive method of screening a cardiac allograft recipient for being at-risk for developing cardiac allograft vasculopathy (CAV), Major Cardiac Events (MACE), and Graft Failure Due to CAV (GFDCAV) of the present disclosure, the method comprises the steps of measuring an amount of a first natural antibody within at least one biological sample from a cardiac allograft recipient; comparing the amount of the first natural antibody in the biological sample with the amount of the first natural antibody in a control sample; wherein a decrease in the amount of the first natural antibody in the biological sample from the cardiac allograft recipient as compared to the amount of the first natural antibody in the control sample indicates a diagnosis of the allograft recipient being either at-risk for or developing cardiac allograft vasculopathy (CAV), Major Cardiac Events (MACE), and Graft Failure Due to CAV (GFDCAV); and selectively enhancing a natural antibody-mediated immune response, further comprising increasing levels of immunoglobulin M and/or immunoglobulin G anti-phosphorylcholine natural antibodies in the allograft recipient's serum, to reduce risk factors of Cardiac Allograft Vasculopathy (CAV), Major Cardiac Events (MACE), and Graft Failure Due to CAV (GFDCAV).

In an exemplary embodiment of a noninvasive method of screening a cardiac allograft recipient for being at-risk for developing cardiac allograft vasculopathy (CAV), Major Cardiac Events (MACE), and Graft Failure Due to CAV (GFDCAV) of the present disclosure, the step of increasing levels of immunoglobulin M and/or immunoglobulin G anti-phosphorylcholine natural antibodies in the allograft recipient's serum, further comprises reducing thrombosis and inflammation risks.

BRIEF DESCRIPTION OF THE DRAWINGS

The disclosed embodiments and other features, advantages, and disclosures contained herein, and the matter of attaining and/or delivering them, will become apparent and the present disclosure will be better understood by reference to the following description of various exemplary embodiments of the present disclosure taken in conjunction with the accompanying drawings, wherein.

Figure 11:
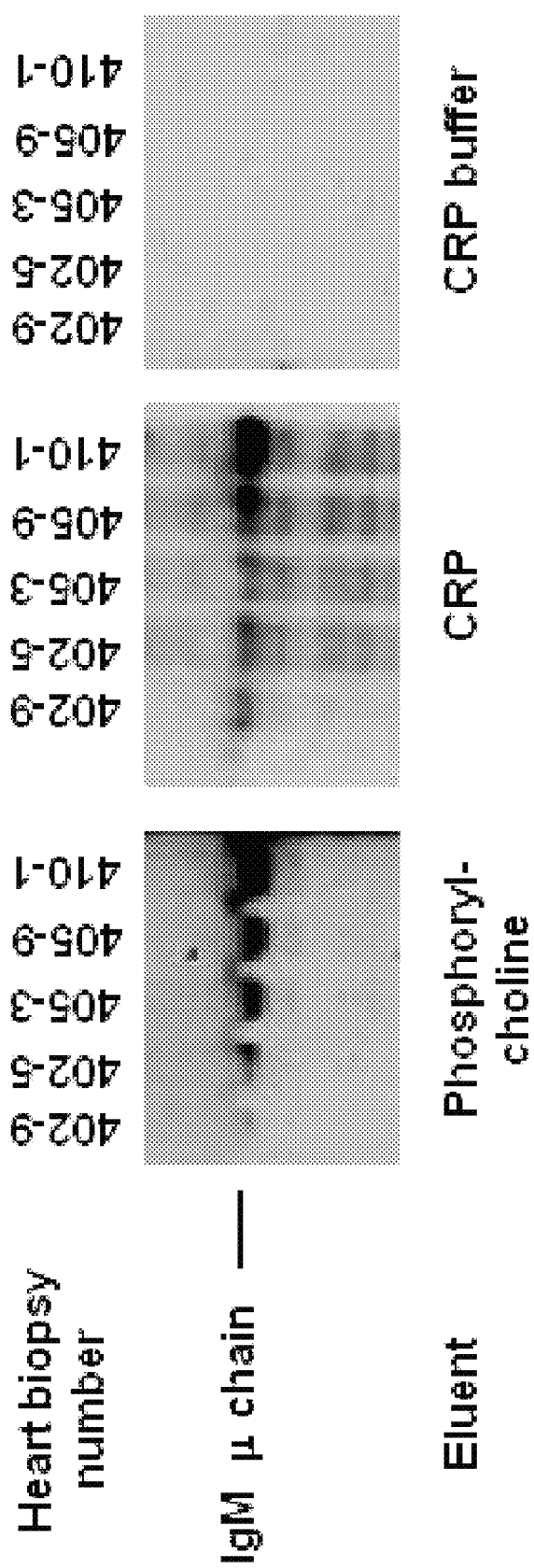
Figure 12:
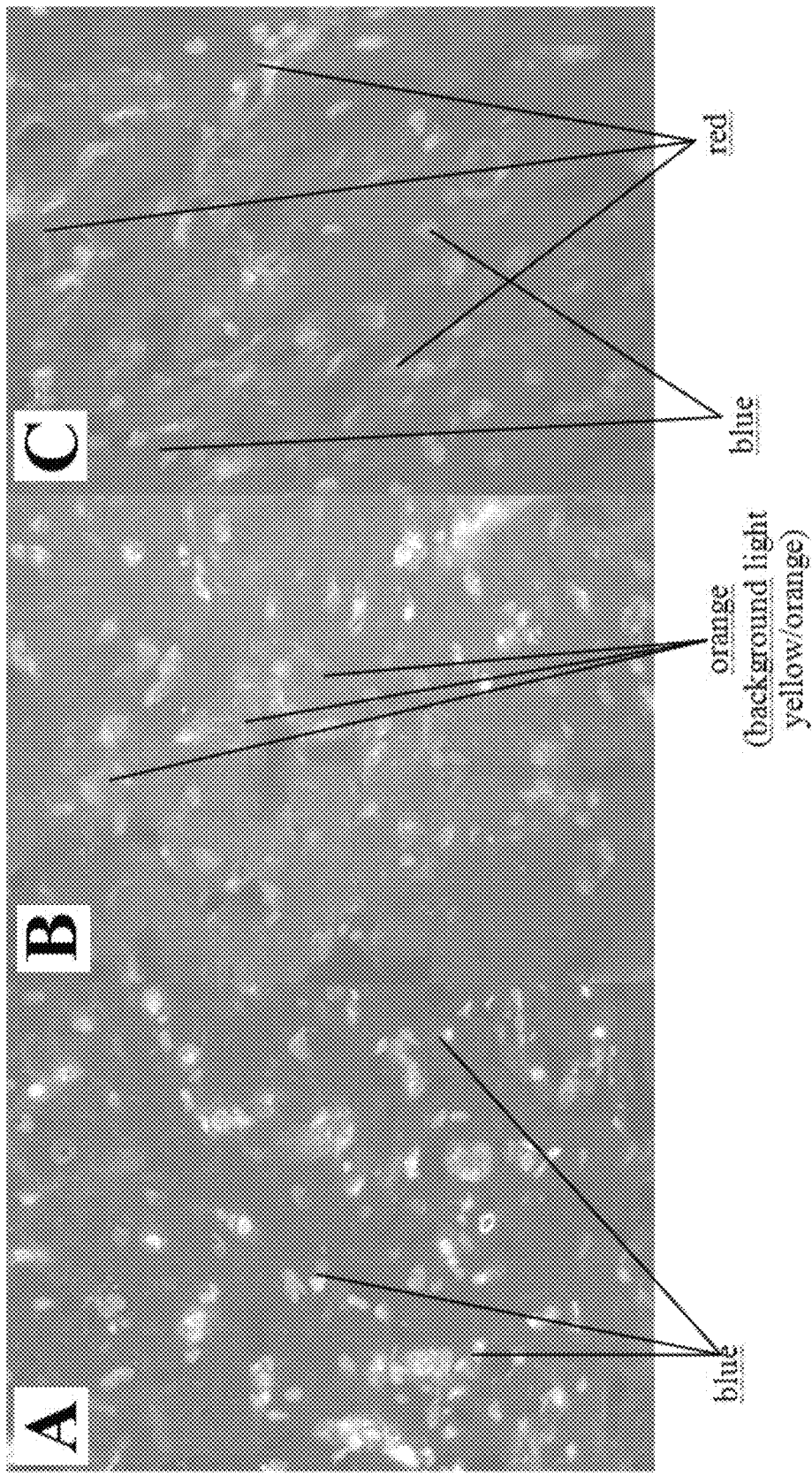

(×5); and photomicrographs from IgM-reacted control (subpart c) and pneumovax 23-vaccinated (subpart d) mouse hearts (×640);

FIG. 11 shows Western blots of eluates obtained from human heart biopsies of transplanted hearts within 6 months post-transplant following incubation of biopsies with PC, CRP, or CRP control buffer;

FIG. 12 shows photomicrographs of the results of displacement experiments; and

Figure 13:
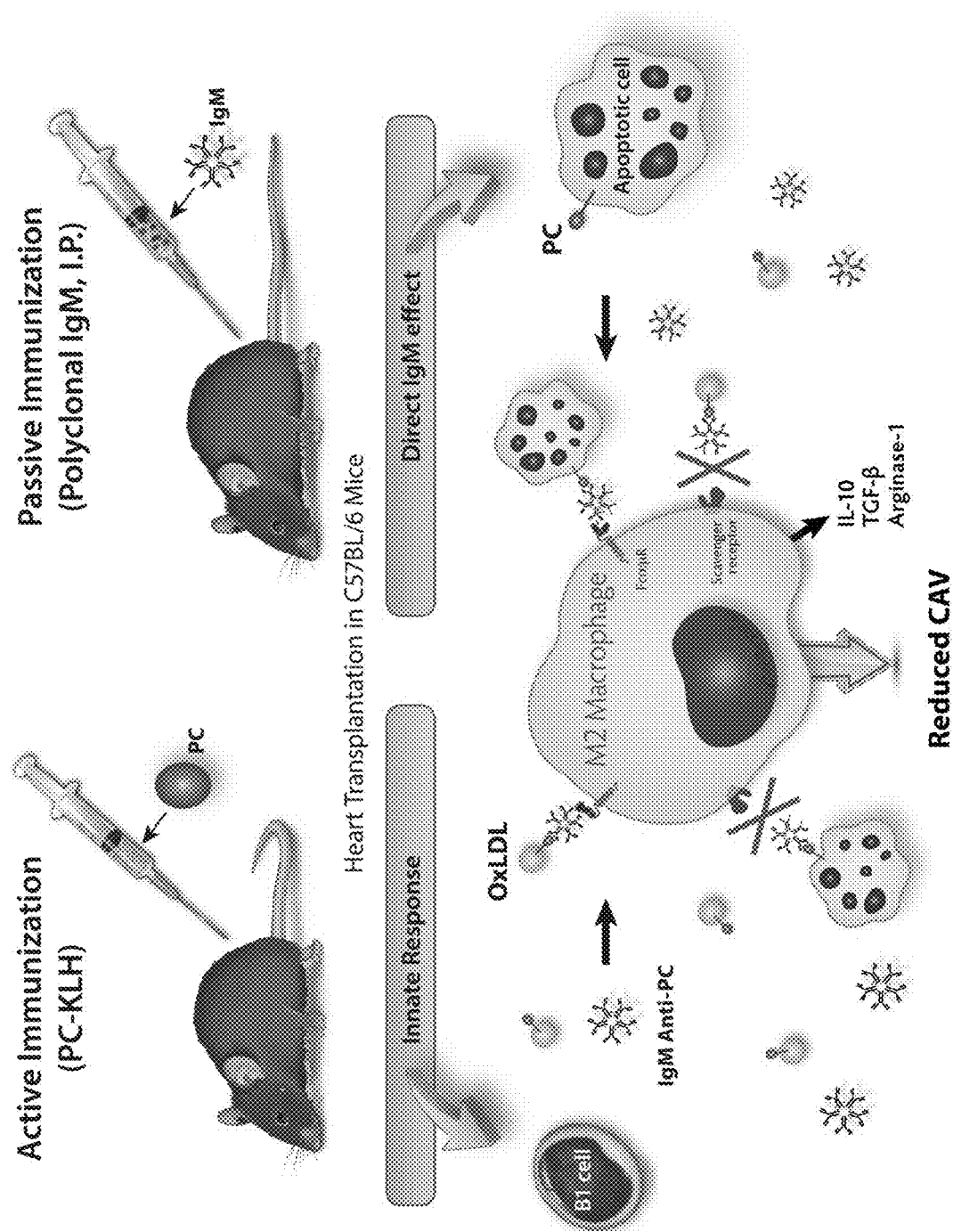

FIG. 13 shows a diagram illustrating how active (PC-KLH) and passive (IgM, I.P.) immunization induces enhanced IgM anti-PC-mediated phagocytosis of apoptotic bodies with M2 MΦ differentiation and reduced CAV.

An overview of the underlying theories, experimental results, features, functions and/or configurations of the vaccines and methods supported by the various figures will now be presented. It should be appreciated that not all of the features of the components of the figures are necessarily described. Some of these non-discussed features, such as various markers, etc., as well as discussed features are inherent from the figures themselves. Other non-discussed features may be inherent in component geometry and/or configuration.

DETAILED DESCRIPTION

Reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. Likewise, while this technology may be illustrated and described in one or more preferred embodiments, the substances and methods hereof may comprise many different configurations, forms, materials, and accessories. For example, while the novel substances, methods and techniques of the present application may be described in the context of identifying early risk predictors for, diagnosing, preventing, and treating cardiac allograft vasculopathy (CAV), the inventive concepts underlying the substances and methods hereof need not be limited to cardiac allografts and may be applied to other medical applications related to organ or tissue transplantation (including both acute and chronic rejection diagnosis and treatment). Additionally, while certain parts of the description may focus on a specific natural antibody (NAbs) such as immunoglobulin M (IgM) antiphosphorylcholine (PC) NAbs, the inventive concepts underlying the substances and methods hereof may also be applied to other such antibodies including, without limitation, immunoglobulin G (IgG) isotypes and immunoglobulin A (IgA).

In the following description, numerous specific details are set forth in order to provide a thorough understanding of the present disclosure. Particular examples may be implemented without some or all of these specific details. In other instances, well known delivery, patient-care, and other medical procedures and operations have not been described in detail so as to not unnecessarily obscure the present disclosure.

The disclosure of the present application provides various novel methods, vaccines and substances for reducing the incidence of transplant rejection, including both chronic and acute rejection. Additionally, various novel substances, vaccines, and methods for diagnosing, preventing and managing allograft rejection are disclosed. Said substances and methods, and the underlying understanding of the physiological and biological mechanisms and actions taking place consistent therewith, are based at least in part on the assertion that recipient immunity—particularly innate immunity—plays a beneficial role in preventing chronic rejection Specifically, unlike conventional methods, the basis of the inventive substances, vaccines and methods of this disclosure considers that specific components of innate immunity play a protective role in preventing allograft rejection in transplant patients. The therapeutic implications of such a consideration is that, in conjunction with the standard approach of suppressing T-cell populations to combat early rejection, relevant components of innate immunity should be enhanced and not suppressed as is currently taught in the medical arts to prevent or delay late rejection. Indeed, the substances, vaccines and methods of the present disclosure focus on enhancing portions of an allograft recipient's innate immune system through therapies designed to enhance the recipient's own serum levels of a specific immunoglobulin M (IgM) and/or immunoglobulin G (IgG) natural antibodies (NAbs) and, thus, enhance his or her antibody-mediated response. Additionally, the diagnostic methods described herein do not have the limitations associated with conventional diagnostic methods such as being invasive, being limited to portions of a patient's vasculature, and/or lacking the requisite sensitivity to detect early stage chronic allograft rejection or patients who are merely at-risk for developing the same.

The novel substances, vaccines, and methods hereof evolved in view of detailed research directed towards understanding chronic rejection following heart transplantation—or CAV. Chronic rejection in the form of CAV is one of the major factors that affects long-term graft and patient survival after heart transplantation. For example, 10-20% of recipients have angiographic evidence of CAV in the first year post-transplantation. Thereafter, CAV increases about 10% per year and, at 5 years post-transplantation, around 50% of heart transplant patients have some evidence of CAV, which is one of the leading causes of death with a 2-year survival rate of less than 15% in those with extended disease.

CAV is an accelerated form of atherosclerosis that narrows the coronary arteries of the transplanted heart. Indeed, atherosclerosis is histopathologically indistinguishable from CAV. Over the last twenty years, medical practitioners and researchers have explored two major questions regarding CAV—namely, (1) What are its precursors?, and (2) What can be done to prevent the development of those precursors? In answer to the first question, the precursors of CAV have been identified to include markers of endothelial activation, coagulation and chronic inflammation. In addition, the normally thromboresistant microvasculature becomes prothrombotic following heart transplantation as a consequence of peri-operative ischemic damage, reperfusion injury, and graft rejection. These early changes are good individual predictors of long-term CAV and chronic graft failure, suggesting that what occurs in the small microvessels also occurs in larger arteries and may be used as CAV biomarkers. Although a definite well-validated surrogate marker for CAV is not conventionally available, the data suggests that early detection of immune and non-immune factors affecting CAV represents the key strategy for detecting a surrogate. Furthermore, these markers are clinically useful as early risk predictors in identifying those patients who are more susceptible to developing long-term CAV and CAV-associated allograft failure (i.e. chronic rejection).

While multiple factors contribute to the development of CAV in heart transplant patients, immunologic mechanisms play the predominant role in the chronic rejection process. Specifically, heart transplantation is associated with ischemia/infarction and induces inflammation, cytokine release, and C-reactive protein (CRP) production, all of which are related to immune response, promote the development of CAV, and further facilitate the feed-forward cycle of inflammation (Fc alpha/mu receptor (Fcα/μR)). However, anti-inflammatory molecules, such as IgM NAbs, are CAV protective by inducing M2 macrophage differentiation/polarization (described below) to break the cycle of inflammation. Accordingly, with regard to the second question (how to prevent the CAV precursors from developing), as previously noted, the present disclosure contemplates that the recipient's innate immune system plays a beneficial role in preventing CAV. This paradigm, at least in part, evolved from the finding that IgM NAbs prevent the formation of native atherosclerosis in atherosclerosis-prone mice.

A. CRP

Traditionally, CRP has been known to be an important risk factor for native atherosclerosis and native coronary artery disease. Elevated CRP plasma levels predict cardiovascular events among apparently healthy men and women, patients with stable and unstable angina, and patients with a previous history of myocardial infarction. Elevated CRP serum levels may promote atherosclerosis through its effect on adhesion molecule expression, since it has been shown that CRP induces ICAM-1 expression in coronary artery endothelial cells. Pro-inflammatory molecules such as CRP can also down regulate tissue plasminogen activator (tPA). Furthermore, possible links between CRP and adhesion molecule expression and between CRP and atherosclerosis have been reported.

Indeed, the present disclosure identifies a strong association between high circulating levels of the pro-inflammatory molecule CRP, a major component of the innate immune system in humans, and a) endothelial activation, and/or b) the development and progression of native atherosclerosis, CAV and, ultimately, graft failure in heart transplant recipients. Specifically, CRP promotion of CAV leads to increases in interleukin-6 (IL-6), interleukin-1β (IL-1β), tumor necrosis factor-α (TNF-α), interleukin-12 (IL-12), and/or even additional CRP, which individually or collectively (such as with two or more of the foregoing) can lead to myocardial infarction, ischemia, and/or inflammation in connection with transplantation. Because said negative effects can also lead to increases/releases of IL-6, IL-1β, TNF-α, and/or additional CRP, a feed-forward inflammation cycle is created thereby even further increasing production of pro-inflammatory cytokines and ever increasing inflammation.

B. Macrophage Polarization

The effect of CRP on inflammation and atherosclerosis is supported by recent findings regarding CRP's influence on macrophage differentiation or polarization. Macrophages (MΦs) themselves are essential players in the development and progression of native atherosclerosis and CAV in heart transplant patients. Furthermore, MΦs can be phenotypically polarized by the microenvironment to mount specific functional programs. Polarized MΦs can be broadly classified into two main groups: 1) classically activated "killer" macrophages (M1), whose prototypical activating stimuli are interferon gamma (IFN-γ) and lipopolysaccharides (LPS); and 2) alternatively activated "repair" macrophages (M2) that function in constructive processes like wound healing and tissue repair. However, separating MΦs into only M1 and M2 phenotypes risks oversimplification of a dynamic continuum of the diverse phenotypes involved in tissue remodeling. To date, M2 MΦs have been further subdivided into M2a (after exposure to interleukin (IL)-4 or IL-13), M2b (after exposure to immune complexes in combination with IL-1β or LPS), and M2c (after exposure to IL-10, transforming growth factor (TGFβ) or glucocorticoids), each with different functions.

Arginine metabolism governs the nature of MΦ activation. In classical (M1) MΦ activation, INF-γ and LPS are classic stimulators of nitric oxide (NO) synthesis from L-arginine, which is mediated by inducible nitric oxide synthase (iNOS or NOS2). Thus, NOS2 is responsible for the production of reactive nitrogen intermediates (RNI) that make reactive oxygen intermediates (ROI). ROI are toxic to pathogens and part of an infection defense mechanism.

Figure 1:
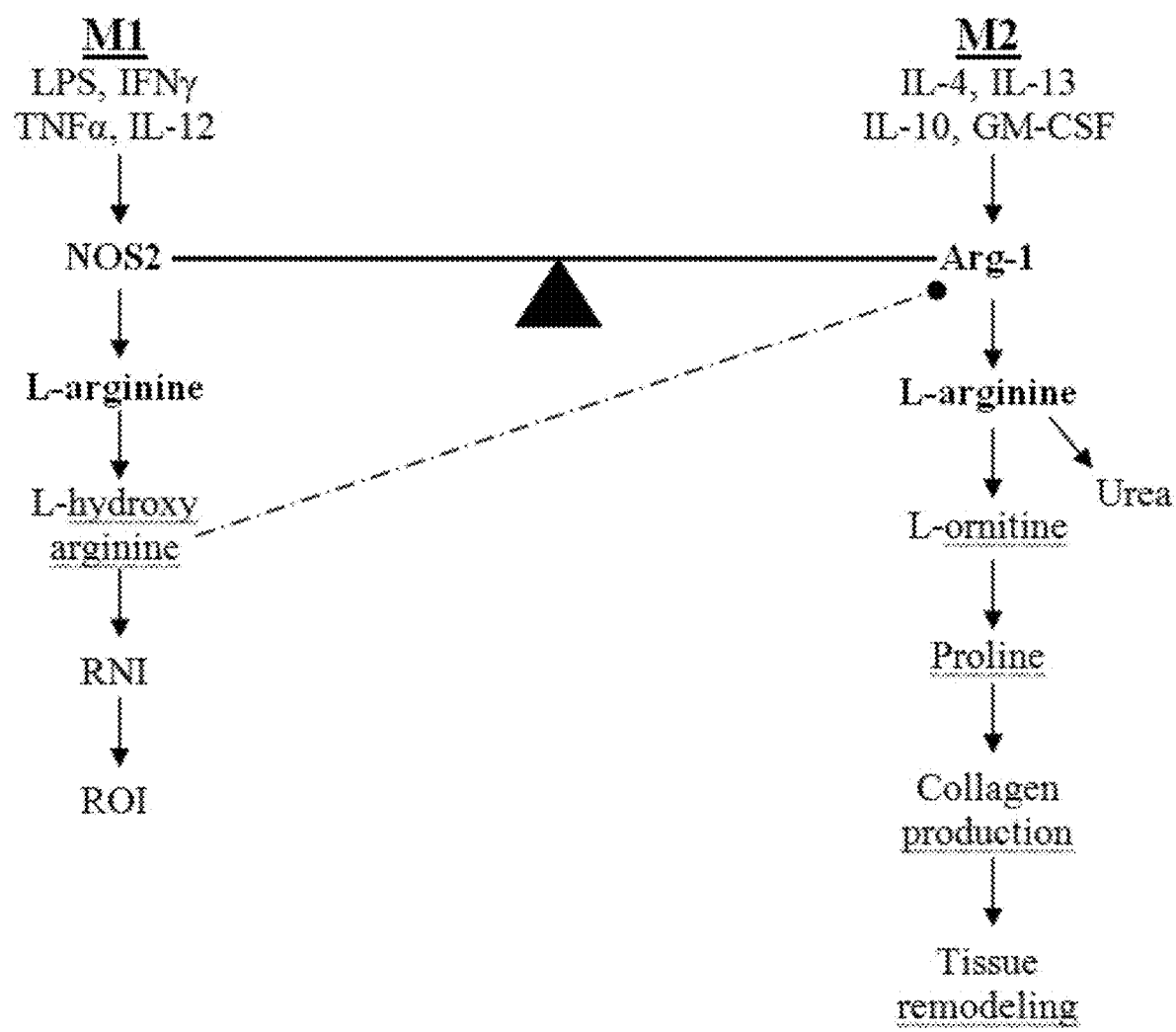
FIG. 1 shows a schematic of Arginine metabolic pathways in macrophages.

In contrast, IL-4 and IL-13 are classical stimulators of L-Arginase-1 (Arg-1), an enzyme that directs L-arginine metabolism through synthesis of L-ornitine and polymers that block NOS2 production. Because L-ornitine is required for proline production, which controls collagen synthesis, Arg-1 activity is associated with tissue remodeling and fibrosis. Since NOS2 shares L-arginine as a substrate with Arg-1, substrate depletion by either enzyme is a key regulatory mechanism. Accordingly, both NOS2 and Arg-1 are involved in the regulation of MΦ effector mechanisms (FIG. 1). Indeed, NOS2 and Arg-1 are markers of M1 and M2 MΦ activation, respectively and M2 MΦs express Arg-1 and no NOS2, while M1 MΦs express arginase-2 (Arg-2) and iNOS, but not Arg-1.

In addition to the foregoing, M1 MΦs promote strong IL-12-mediated Th1 responses and appear to have two harmful effects on a transplanted graft: 1) they develop into lipid-engorged foam cells that become trapped in the vessels and contribute to endothelial activation and the accumulation of arterial plaque; and 2) they generate pro-inflammatory cytokines that further promote the inflammatory milieu and induce further production of harmful M1 MΦ. By contrast, M2 MΦs promote Th2-associated effector functions and produce high levels of anti-inflammatory cytokines like IL-10, which play a role in the resolution of inflammation through high endocytic clearance capacities and reduced pro-inflammatory cytokine secretion. Referring back to CRP, it has been shown that CRP increases M1 MΦ polarization (tumor necrosis factor [TNF]/IL-12/C-C chemokine receptor 2, TNF/IL-12/monocyte chemotactic protein-1, or TNF/IL-1/IL-12) and induces the conversion of M2 MΦ into the M1 phenotype.

C. NAbs

Anti-inflammatory molecules, such as IgM and/or IgG natural antibodies (NAbs), another component of the innate immune system, reduce the effect of pro-inflammatory molecules (such as a CRP) and block foam cell formation by polarizing the MΦs toward the beneficial anti-inflammatory M2 subtype and, thus, breaking the cycle of inflammation. This causes the MΦ to release anti-inflammatory cytokines and promotes MΦ clearance, thereby preventing their accumulation in the vessel wall. As such, NAbs convey an atheroprotective function, and high titers of IgM and/or IgG NAbs have been associated with reduced atherosclerosis.

Figure 2:
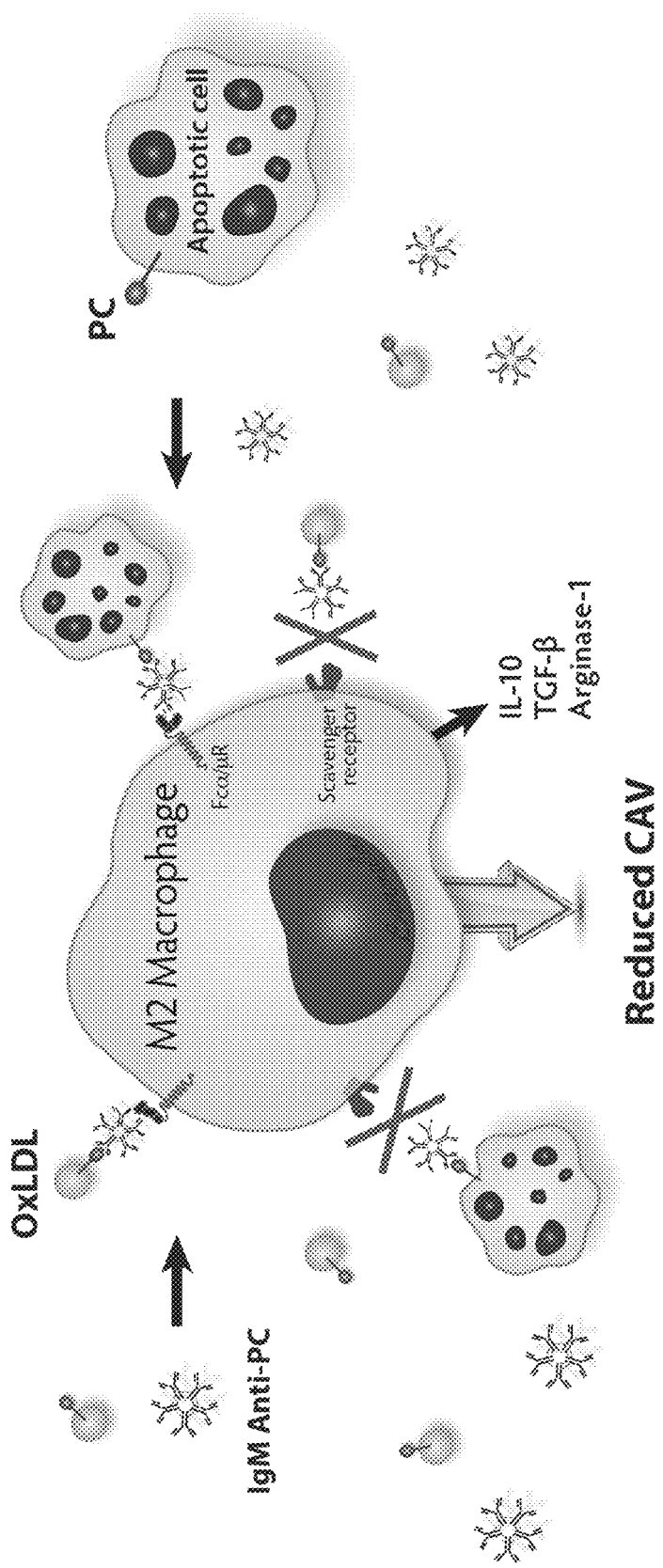
FIG. 2 shows a diagram illustrating a mechanism through which IgM anti-PC NAbs block oxidation-specific epitopes in oxLDL and apoptotic cells and induce favorable M2 macrophage (MΦ) polarization to clear the transplanted organ of pro-inflammatory agents. OxLDL: oxidized low-density lipoprotein; IL-10: Interleukin-10; TGF-β: Transforming growth factor-beta; cardiac allograft vasculopathy: CAV.

It is known that innate immunity, in the form of at least IgM NAbs, prevents the formation of native atherosclerosis in atherosclerosis-prone mice and that innate NAbs are present even in naïve germ-free mice in the absence of exogenous antigen exposure. Indeed, NAbs anti-PC constitute between about 5-10% of the total IgM pool. However, conventionally, the relationship between IgM NAbs, pro-thrombotic graft vasculature, and pro-inflammatory molecules like CRP, as well as the relationships between these factors and the subsequent development and progression of CAV and graft failure in humans, has been unclear. It has been proposed that the NAbs confer their atheroprotective effect by responding to oxidation-specific epitopes (damage-associated molecular patterns or DAMPs) that constitute a "self-altered" danger signal, occurring as a result of oxidative stress. Oxidative stress can arise when cells undergo apoptosis (resulting from endothelial injury) or in association with endothelial accumulation of oxidized low-density lipoprotein (oxLDL). Either or both of these events can occur within the allografts of organ transplant recipients. With normal-high levels of IgM NAbs (for example), once these damaged cells are recognized, they are cleared by IgM NAbs before they can accumulate to form atherothrombotic plaque (see FIG. 2).

An early precipitating event in organ transplantation, as referenced herein, may be related to reperfusion injury occurring during, or immediately following, the transplant operation, which ultimately leads to DAMPs formation. Interestingly, low levels of IgM anti-phosphorylcholine (PC) NAbs are associated with the development of atherosclerosis in hypertensive individuals, as well as with the increased prevalence of vulnerable plaques in patients with systemic lupus erythermatosus where low levels of anti-PC NAbs independently predict development of cardiovascular disease. Likewise, it has been found that low levels of anti-PC IgM are associated with an increased incidence of cardiovascular disease and stroke. Accordingly, in at least one exemplary embodiment of a method of this disclosure, low levels of anti-PC antibodies can be used to independently predict the development of cardiovascular disease in a patient. As atherosclerosis is histopathologically indistinguishable from CAV, the present disclosure includes disclosure of reducing or even eliminating an incidence of allograft/transplant rejection (against the development of CAV or chronic rejection in other solid organ transplants) based at least in part upon the same innate immune response. As a means of comparison, it has been shown that samples from clinically normal controls typically have NAbs levels between about 20 units/ml and about 60 units/ml.

Furthermore, the disclosure of the present application identifies that active immunization with PC and passive immunization with anti-PC ameliorate atherosclerosis development, and passive immunization with anti-PC IgM significantly reduces vein graft lesion size and inflammation in mice. These beneficial effects may be related to the capacity of IgM NAbs to remove the accumulation of cells undergoing apoptosis, the accumulation of endothelial oxLDL, or both. The disclosure of the present application identifies that a NAbs' response to oxidation-specific epitopes (endogenous DAMPs) in apoptotic cells of heart transplant recipients protects against CAV by producing a polarized M2 MΦ-mediated resolution of inflammation. This disclosure has been formulated on the basis of (1) experimental results showing that high IgM deposits in transplanted human heart microvessels are associated with reduced CAV and allograft failure (and vice versa), and that microvascular myocardial IgM can be eluted from biopsies with PC and CRP, (2) preliminary data showing that pneumococcal vaccination in mice induces IgM anti-PC NAbs and reduces atherosclerosis; and (3) studies showing that high IgM anti-PC NAb levels are associated with reduced vein graft plaque in mice and reduced atherosclerosis in mice and humans. As discussed in further detail below, understanding the role of IgM NAbs in CAV can lead to new therapeutic strategies that exploit such NAbs in connection with inducing recipient antibody production, which may potentially protect transplanted tissue and improve patient outcomes.

The present disclosure bridges the effects of IgM and/or IgG anti-PC antibodies in facilitating MΦ phagocytosis of apoptotic cells through alternative MΦ-activation subtypes. Clinically, these findings provide a basis for a fundamentally new approach to patient diagnosis and ultimately management using novel therapies designed to enhance the recipient's own IgM and/or IgG anti-PC antibody-mediated response. The novel rationales of the present disclosure reverse the paradigm of immunosuppression to prevent graft rejection by singling out and enhancing specific components of immunity that may be beneficial in controlling inflammation and preventing graft rejection, thus opening a fundamentally new avenue for current diagnosis of CAV and future research designed to improve heart allograft survival. The present disclosure combines well-established methods with novel approaches to a critically important problem in transplantation research in particular, and atherosclerosis in general.

As referenced in further detail herein, a determination is made as to whether specific components of innate immunity, IgM and/or IgG anti-PC, play a protective role by preventing or delaying CAV onset, thereby reducing the incidence of graft failure and death. The present disclosure is scientifically significant and clinically translational because it provides evidence for the following: 1) that high levels of serum NAbs are associated with a reduced incidence, or delayed onset, of late (chronic) rejection following human heart transplantation which becomes a powerful biomarker for the status of the graft, 2) the protective effect can be induced experimentally in an in vivo heart transplant model using a PC vaccine, and 3) the underlying mechanism for this protection is an effect of IgM/IgG anti-PC on macrophage polarization and endothelial cell activation.

The present disclosure further identifies the role of IgM and IgG anti-PC in protecting tissue allografts against chronic rejection through its effects on MΦ differentiation or polarization and subsequent clearance of damaged or apoptotic cells. As previously described in detail, polarized macrophages can be broadly classified into two main groups: 1) classically activated macrophages (M1); and 2) alternatively activated macrophages (M2), with M1 MΦ promoting strong IL-12-mediated Th1 responses and M2 MΦ promoting Th2-associated effector functions that play a role in the resolution of inflammation. By identifying specific gene signatures associated with MΦ polarization, the present disclosure newly explores the protective function of these cells as part of a NAb-mediated response against chronic allograft rejection. The innovative feature of this research lies in its potential to open a fundamentally new clinical approach to diagnosis, including the prevention and management of chronic allograft rejection. The basic mechanism defined herein, linking IgM and/or IgG NAbs to the M2 beneficial form of MΦ polarization, can be further exploited to develop and test a novel therapeutic approach to chronic allograft rejection—an approach that would seek to enhance (for example, via vaccination) the beneficial components of a recipient's own NAb-mediated response to a foreign tissue allograft. The studies and disclosure referenced herein are innovative because they focus on an understanding of the protective effect of innate immunity on CAV and the role that MΦ polarization plays in such protection that has clinical translation. The results of the studies and the present disclosure will have an important positive impact by immediately establishing a fundamentally new diagnostic and a novel therapeutic strategy for protecting transplanted organs by enhancing the recipient's own IgM and/or IgG NAb-mediated response.

The role of innate immunity in the prevention or inhibition of CAV and graft failure represents a promising avenue for investigation, especially regarding the identified beneficial role that the early presence of IgM NAbs has following heart transplantation through preventing and/or delaying the development of CAV and graft failure. Contrary to several reports in humans showing that IgM autoantibodies, in general, are associated with accelerated or more severe CAV and graft failure, previously published research suggests that higher IgM antibody tissue and serum levels, as well as higher IgM anti-PC serum levels, are associated with beneficial outcomes (i.e., reduced CAV and prolonged graft survival).

It has been newly determined that a significant relationship exists between serum levels of anti-PC NAbs and subsequent downstream events in heart transplant patients, including incidence rates of chronic rejection (or CAV), graft failure, major adverse cardiac events, and death. More specifically, data suggests that IgM antibodies, for example, play a protective role in transplanted human heart patients, protecting the graft against CAV by inducing a polarized M2 MΦ-mediated resolution of inflammation. For example, as described herein, the presence of increased levels of specific IgM/IgG anti-PC NAb in the serum of human heart transplant recipients is associated with increased microvascular myocardial IgM/IgG, an increased number of M2 MΦs, and reduced signs of inflammation and thrombosis. Supporting this, it has been conversely shown that patients lacking IgM atheroprotection have low levels of anti-PC NAbs and exhibit signs of inflammation, an increased number of M1 MΦs, and a prothrombotic and activated microvasculature (which is associated with an increased incidence of CAV and more rapid graft failure).

To gain a better understanding of the mechanism(s) involved in early post-transplant endothelial activation and prothrombogenicity, and the protective effects of IgM NAbs, the prothrombotic status of transplanted hearts was evaluated using immunohistochemistry and antibodies to fibrin, antithrombin and tissue plasminogen activator. For example, in at least one novel attempt to identify the nature of the atheroprotective effect of IgM NAbs in heart transplant patients, the presence of anti-PC NAbs were evaluated in a set of serum samples using a specific enzyme-linked immunosorbent assay (ELISA: CVDefine, Athera). Furthermore, MΦ phenotypes were assessed using 4-color immunohistochemistry and subsequently characterizing M1 polarized MΦs with antibodies to TNF/IL-1/CCR2/IL-12/23 and M2 polarized MΦs with antibodies to CD163/IL-10/CD206. Thereafter, CRP levels were measured using ELISA endomyocardial biopsy intercellular adhesion molecule-1 (ICAM-1) levels with immunohistochemistry. Such evaluations resulted in the identification of new CAV biomarkers, which ultimately led to the development of the novel diagnostic tools and therapies described herein for decreasing CAV and improving survival.

Figure 3:
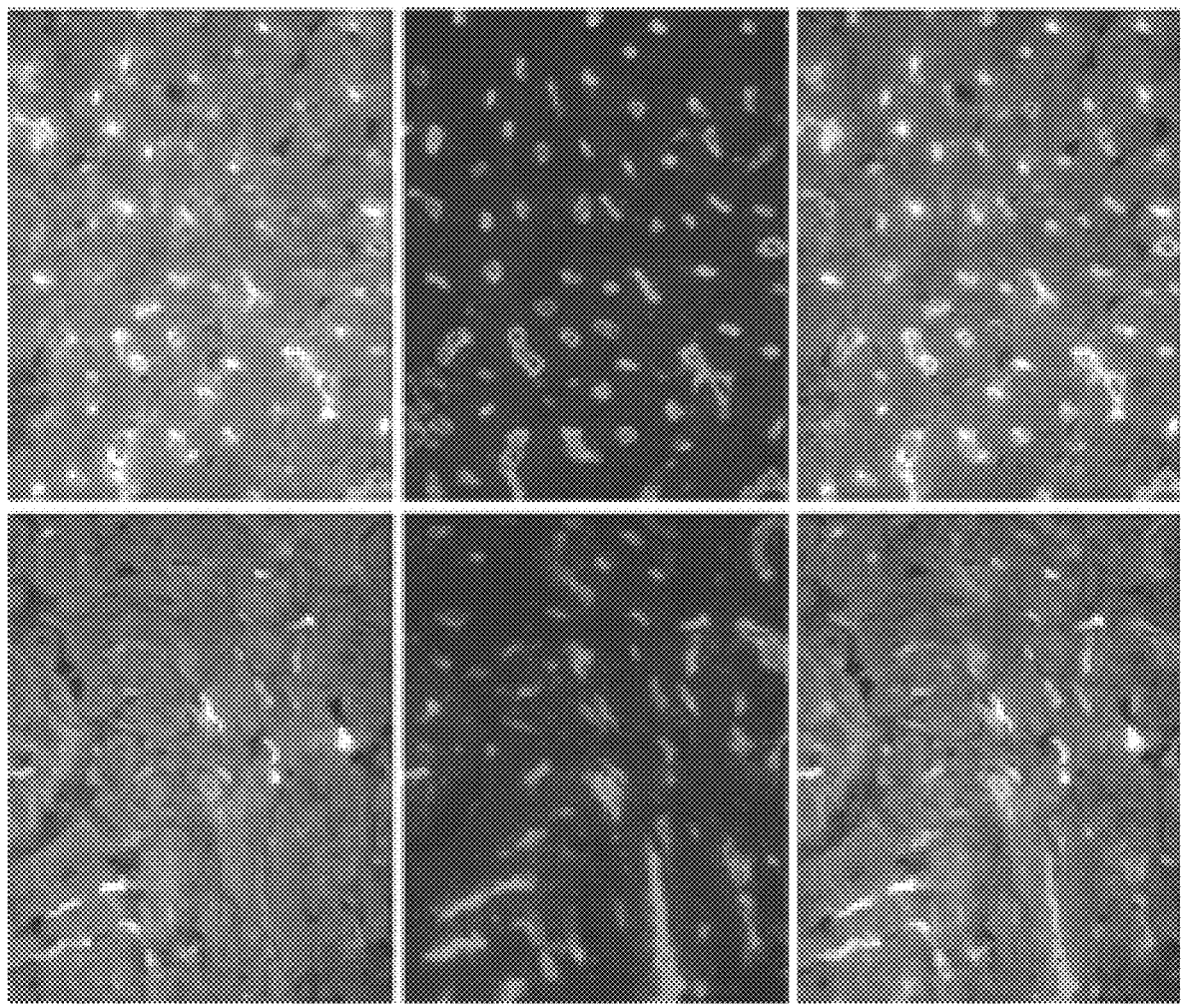
FIG. 3 shows a 640× microscopic view of human heart biopsies showing abundant (top row) and scant (bottom row) IgM capillary reactivity.

Now referring to FIG. 3, six human heart biopsy specimens are shown under magnification. The specimens having an early presence of abundant IgM antibodies within the cardiac microvasculature (FIG. 3, top row) experienced reduced morbidity and mortality as compared with the patients having reduced (or lacking) IgM reactivity. Conversely, a significant link was identified between those specimens with reduced IgM (FIG. 3, bottom row) and subsequent fibrin deposition within the heart, a condition that ultimately has a detrimental effect on allograft and patient survival. It is thought that this relationship stems, at least in part, from the propensity for IgM anti-PC NAbs to induce polarized M2 MΦ-mediated resolution of inflammation by blocking oxidation-specific epitopes in apoptotic cells and oxLDL within the heart transplants.

Because the downstream effects of low NAbs levels are significant, the same can also be used as early biomarkers for identifying negative allograft outcomes. For example, it has been determined that fibrin deposits within graft microvasculature having myocardial damage are evidenced by increased serum cardiac troponin I levels, lack of anticoagulant and fibrinolytic capacity, and/or the up-regulation of endothelial ICAM-1. Accordingly, these downstream events can be analyzed and used as diagnostic tools with respect to screening for the early stages of CAV or chronic allograft rejection.

Figures 4A, 4B:
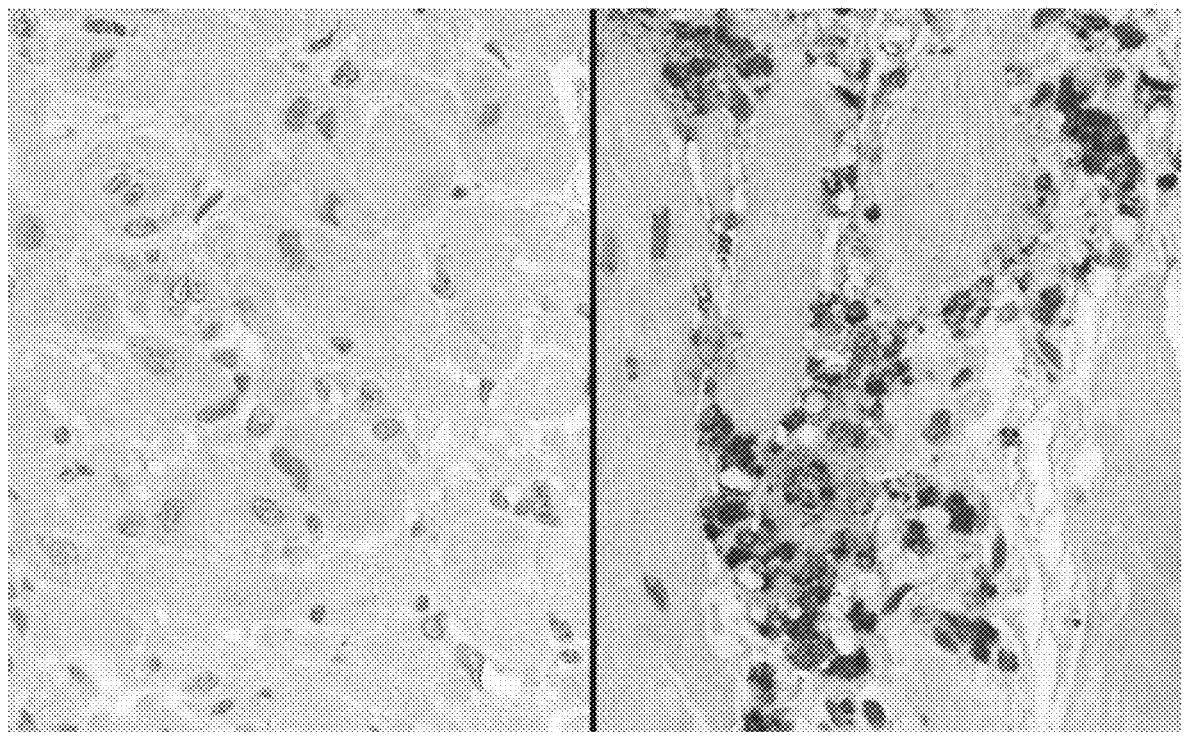
FIGS. 4A and 4B show 640× microscopic views of human heart biopsies reacted with antibody to Arginase 1. Absence of reactivity (FIG. 4A) in donor heart and macrophages reactive (FIG. 4B) in biopsy with IgM reactive capillaries.

The findings set forth herein support that the presence of myocardial IgM (most probably NAbs) is indeed associated with an atheroprotective innate immune response. Additional data has also shown variability in Arginase 1 (an M2 MΦ marker) expression in human heart biopsies from heart transplant patients (FIGS. 4A and 4B). Specifically, human heart biopsies were reacted with an antibody to Arginase 1. The results showed an absence of reactivity in the donor heart (FIG. 4A), while FIG. 4B clearly illustrates MΦs reactivity in a biopsy with IgM reactive capillaries, suggesting that the expression of Arginase 1 can be used to evaluate the relationship with IgM anti-PC levels.

NAbs and B-1 Cell Protective Effector Functions

Additional studies focused on vaccination-based atheroprotection. Specifically, it has been determined that anti-oxLDL IgM NAbs provide atheroprotection through IgM binding to oxLDL and subsequent clearing from circulation. Additionally, NAbs may bind to oxLDL within the arterial intima, forming immune complexes that prevent oxLDL engulfment by macrophages. In this manner, the NAbs limit foam cell formation, which is associated with increased tissue factor-mediated thrombosis in the atherosclerotic plaque.

Mouse B-1 cells are the main producers of NAbs and were first described as a relatively small population of CD5$^+$ splenic B cells that spontaneously secrete IgM. The spleen is a major source of oxLDL-specific IgM in non-immunized atherosclerotic mice. Furthermore, splenectomized mice immunized with pneumococcal extracts do not develop anti-PC responses.

Primarily, the proposal was that sera from PC-vaccinated C57BL/6 mice would induce MΦs following IgM-mediated phagocytosis of apoptotic cells and would subsequently reduce endothelial cell activation in vitro. To confirm that PC-vaccinated mice were able to produce IgM NAbs, studies were performed on LDL-receptor-deficient mice. More specifically, such mice were immunized with Pneumovax 23 to evaluate the effects of vaccination on atherosclerosis development.

Figure 5:
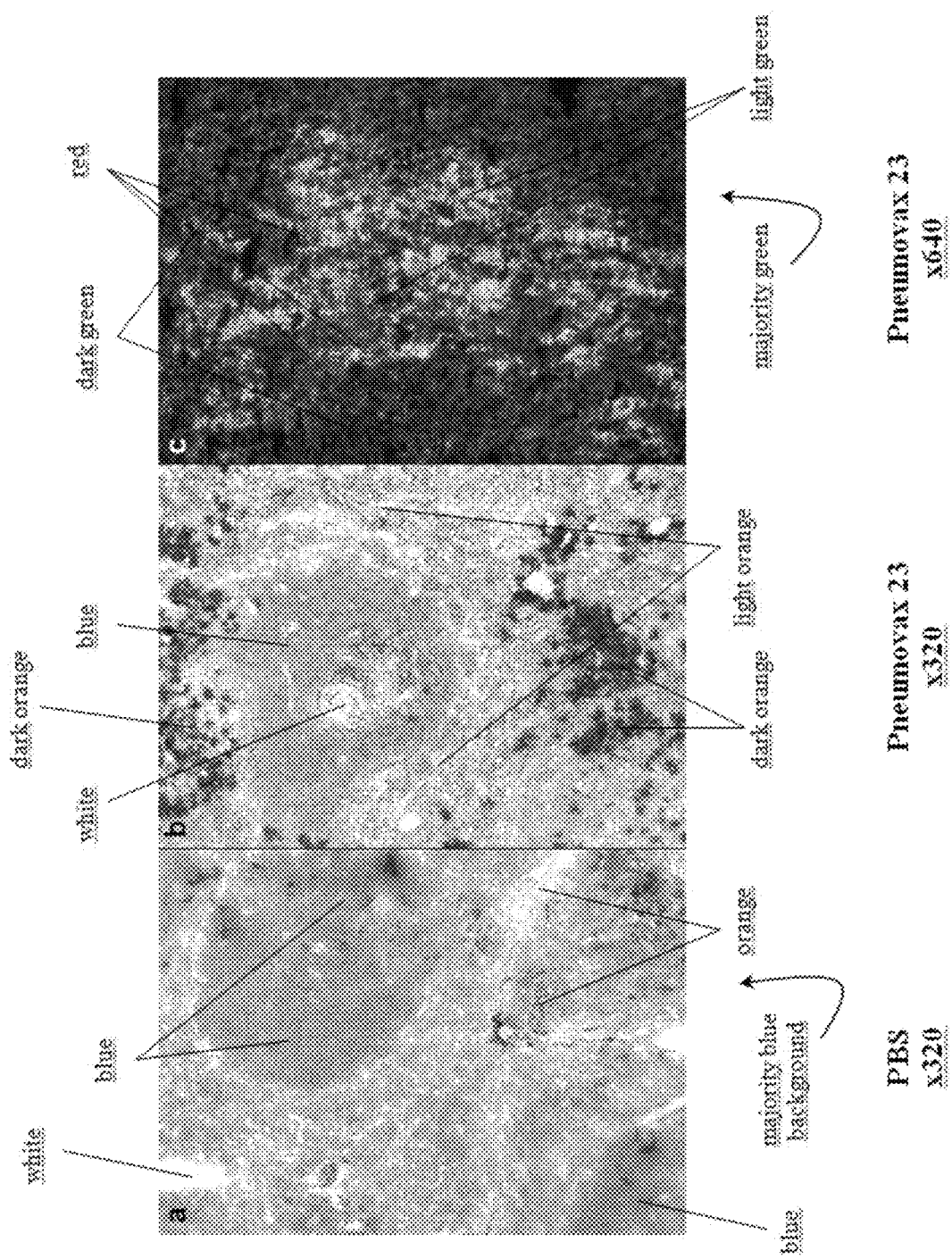
FIG. 5 shows microscopic views of murine spleen biopsies from mice immunized with PBS (left), and Pneumovax 23 (center), evidencing a significant increase of IgM-reactive cells in treated mice vs. controls (X320); Spleen from Pneumovax 23-treated mice (center) showing IgM+(green) and CD5+(red) cells (right); Most cells are orange, confirming IgM+ are also CD5+ cells (X640)

The results of this study showed a significantly higher number of IgM cells in the spleens of vaccinated animals as compared to the controls (FIG. 5). To confirm that the IgM cells were most likely B1a cells, double antibody studies were also performed using an antibody to CD5$^+$. As shown in FIG. 5, there was a significant increase in IgM-reactive cells in treated mice (center) versus the controls (left). Additionally, the splenic cells from the Pneumovax 23-treated mice (FIG. 5, center) showed both IgM$^+$ (green)

and CD5+ (red) cells (right). As most cells are orange in the image on the right, the results confirm that the IgM+ cells were also CD5+ cells.

Figure 6:
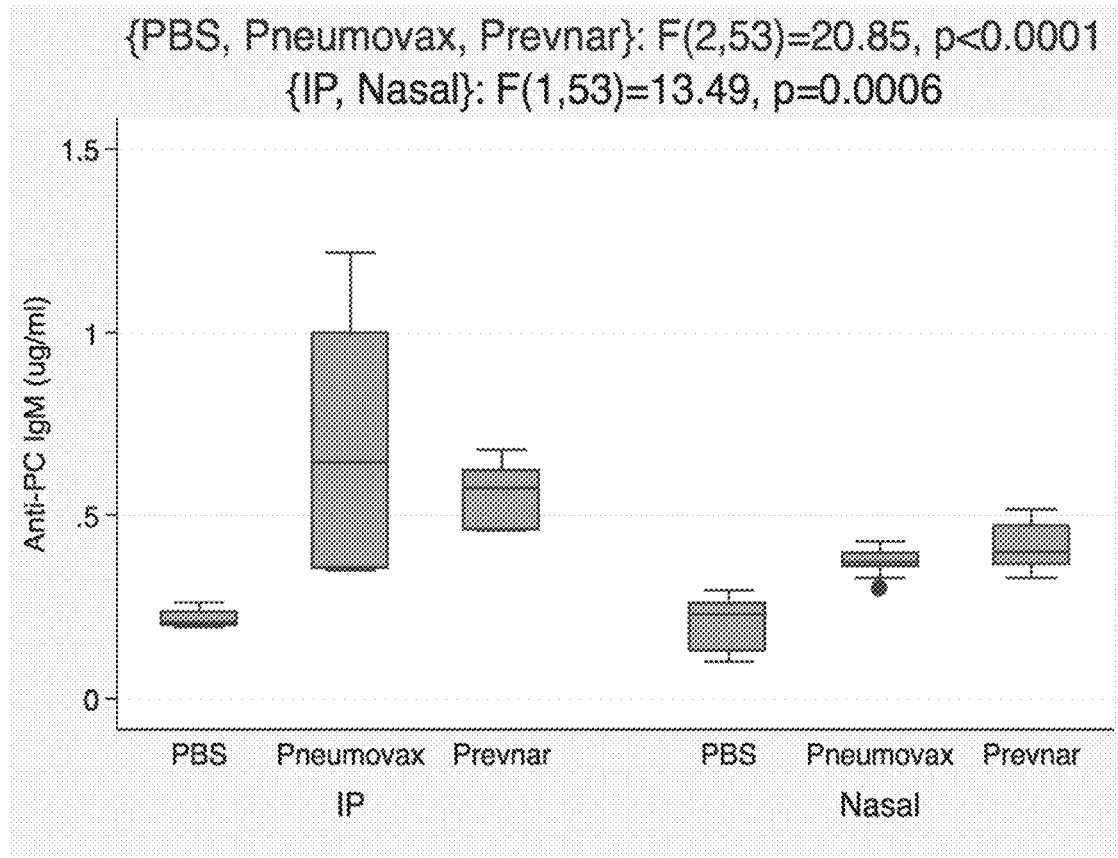
FIG. 6 shows a graphical representation of the resulting anti-PC IgM NAbs production levels after LDL-deficient mice are treated with Pneumovax 23 or Prevnar vaccinations when delivered through intraperitoneal (IP) injections versus nasally.
Figure 7:
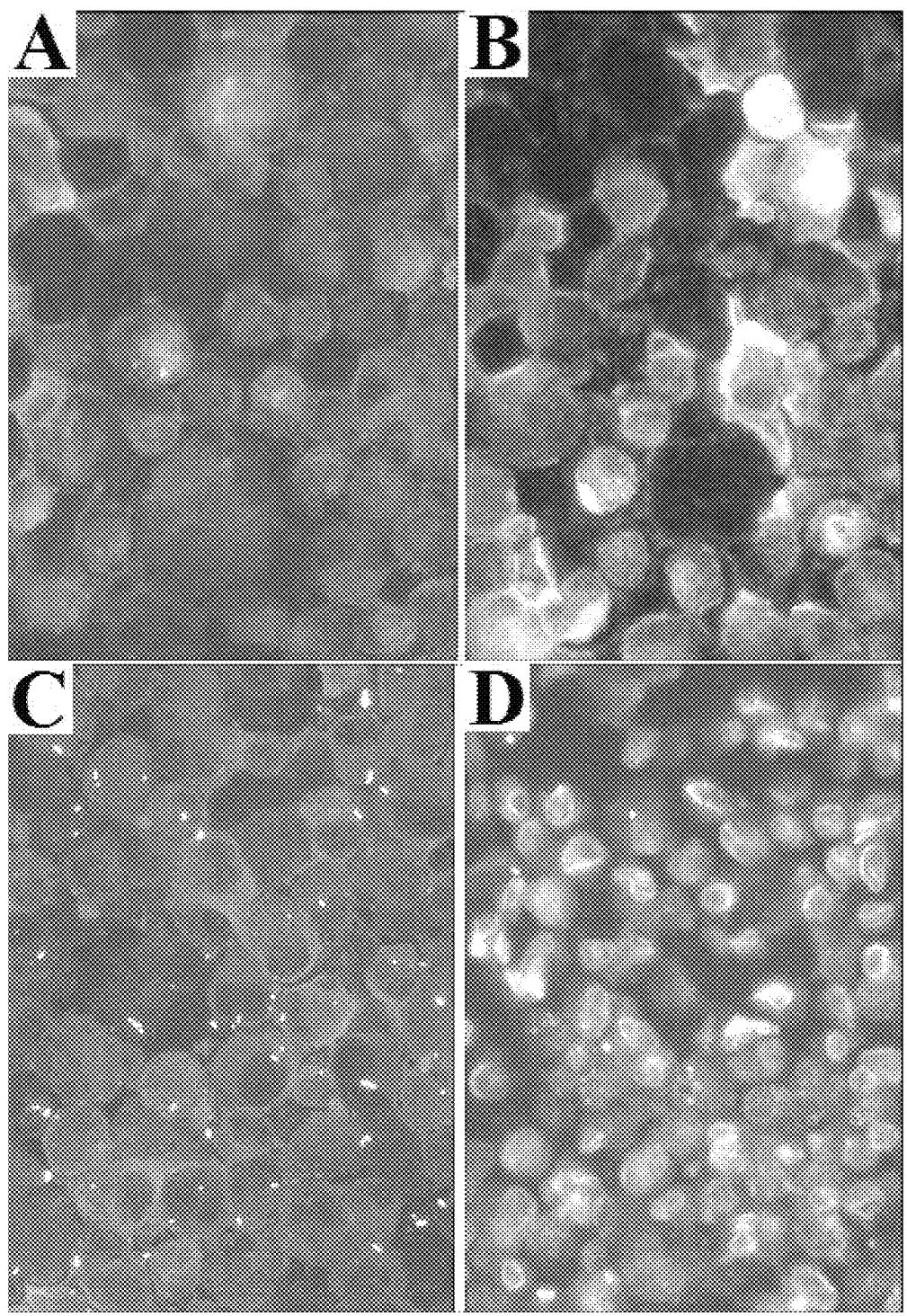
FIG. 7 shows microscopic views of human aortic endothelial cells showing ICAM-1 (subpart B) and NF-κB nuclear expression (subpart D) following incubation with C-reactive protein (CRP); note the absence of ICAM-1 (subpart A) and NF-κB nuclear expression (subpart C) in controls without CRP.

Furthermore, ELISA studies showed that pneumococcal vaccination enhanced IgM anti-PC NAb mouse serum levels as compared to the controls, and intraperitoneal injections were found to be significantly more effective than nasal administration (see FIG. 6). Finally, incubation of cultured human aortic and microvascular endothelial cells with CRP induced cell activation as identified by increased ICAM-1 expression and nuclear factor-kappa B (NF-κB) nuclear localization (FIG. 7). As shown in FIG. 7, the human aortic endothelial cells showed ICAM-1 (subpart B of FIG. 7) and NF-κB nuclear expression (subpart D of FIG. 7) following incubation with CRP. Additionally, note the absence of ICAM-1 (subpart A of FIG. 7) and NF-κB nuclear expression (subpart C of FIG. 7) in the controls that lacked CRP exposure.

In sum, the data from these studies support that mouse immunization with Pneumococcal vaccines induces IgM NAbs. Furthermore, a pro-inflammatory status following incubation with CRP induces cell activation in aortic and microvascular endothelial cells.

As *Streptococcus pneumoniae*'s cell wall, apoptotic cells, and oxLDL share common PC moieties, pneumococcal vaccination can be used to induce the production of anti-PC (T15/EO6) NAbs. Thereafter, LDL oxidation can be used to "expose" the PC moiety, thereby making it an epitope for T15/EO6 NAbs. A protective effect of IgM antibodies was demonstrated in heart transplant patients. Indeed, the early presence of IgM antibodies in the cardiac microvaculature was associated with reduced morbidity and mortality as compared with patients lacking IgM. The hypothesis was that those protective IgM antibodies are directed against PC exposed in microvascular apoptotic cells. To test this hypothesis in vivo, different mouse genotypes were immunized against PC prior to heart transplantation, and whether immunization led to an enhanced NAb response that confers allograft protection was evaluated.

Figure 8:
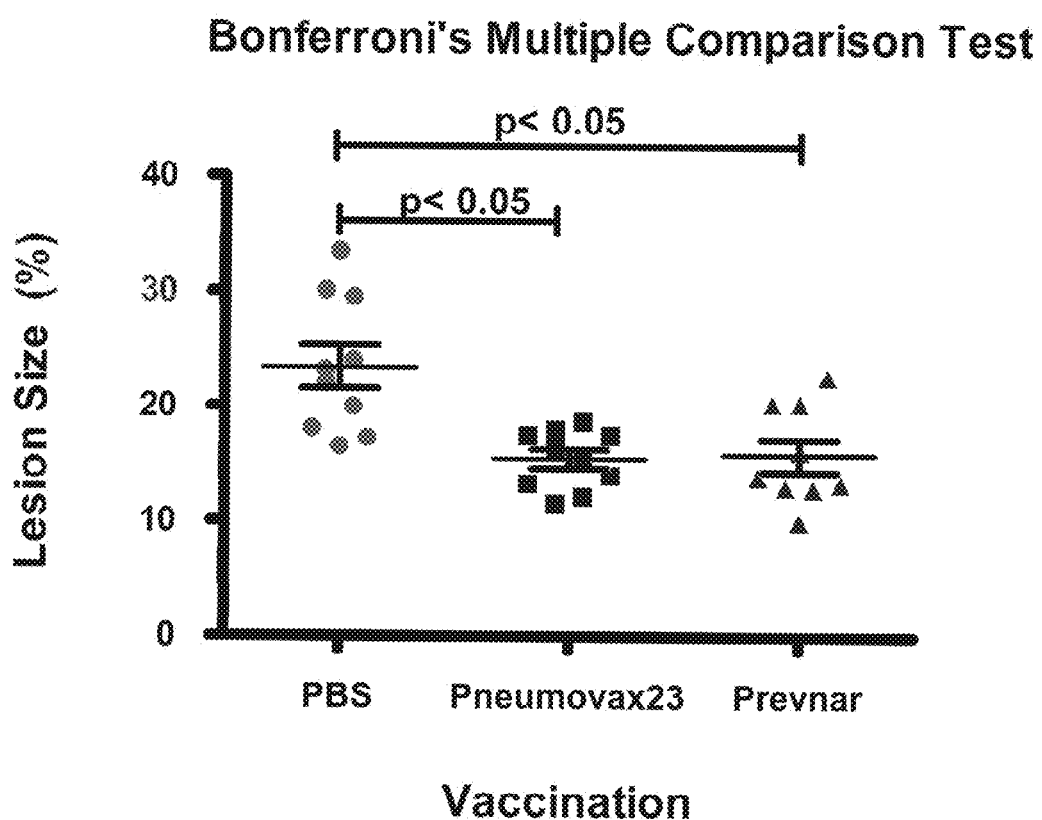
FIG. 8 shows a chart representative of atherosclerosis aortic lesion size reduction after vaccination with Pneumococcal vaccines on LDLR-deficient mice.
Figure 9A:
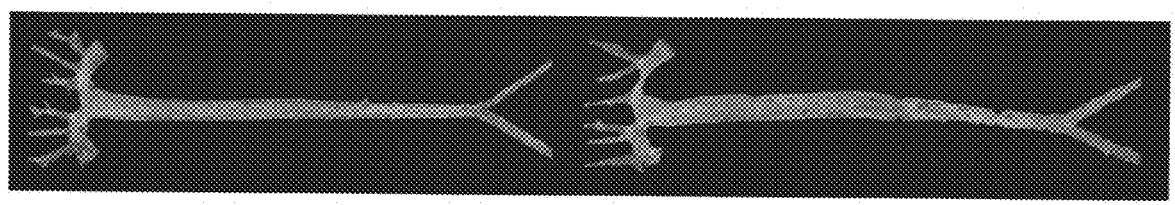
FIG. 9A shows atherosclerosis in Pneumovax 23-treated (left) and control (right) aortas.
Figure 9B:
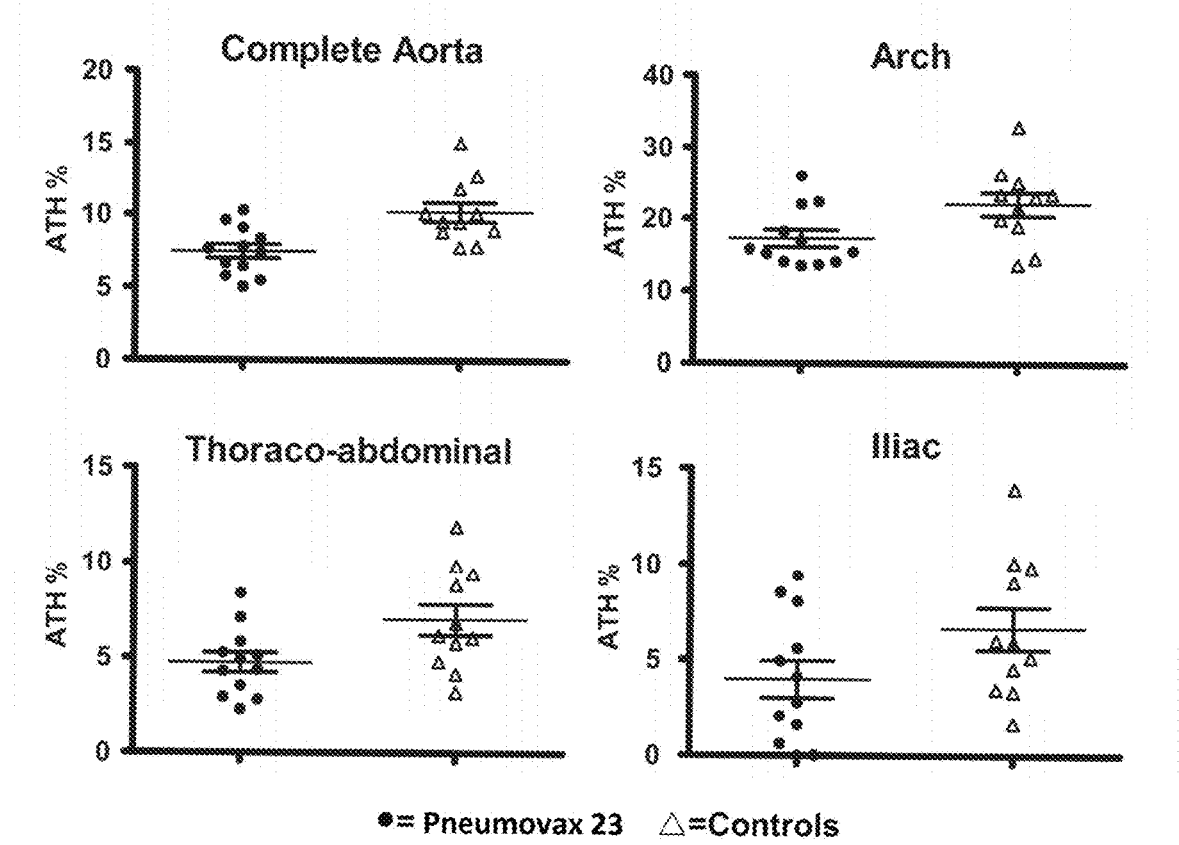
FIG. 9B shows graphical representations of atherosclerotic lesions in complete aorta, arch, thoracoabdominal aorta and iliacs in Pneumovax-23-treated and control animals.
Figure 10:
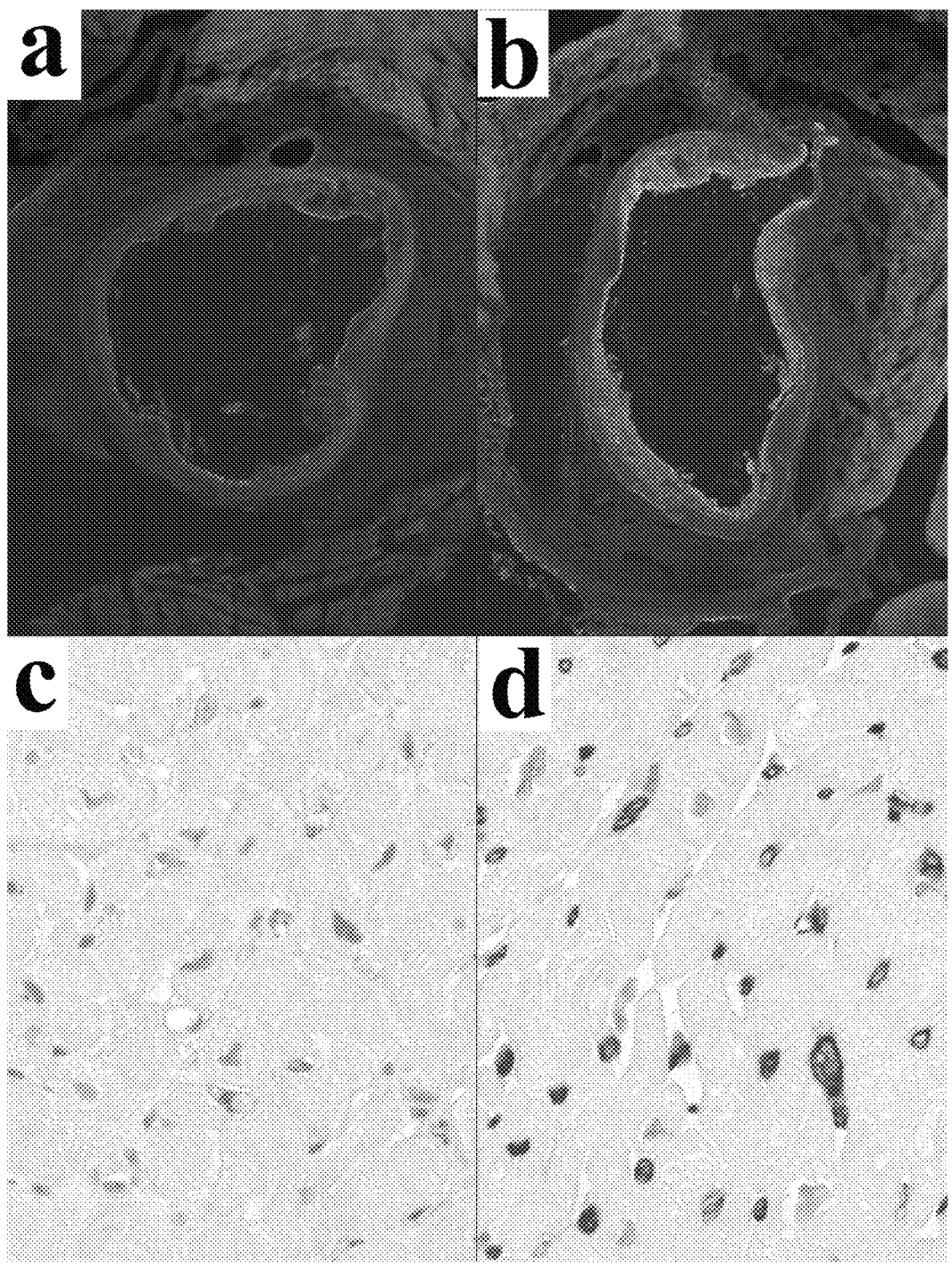
FIG. 10 shows IgM reactivity in aortic roots of control (subpart a); Pneumovax 23-vaccinated mice (subpart b)

Supporting the hypothesis, preliminary studies showed that immunization with pneumococcal vaccines (Pneumovax 23 and Prevnar) of LDLR-deficient mice fed with a high-fat, high-cholesterol diet significantly reduced aortic atherosclerotic lesion size (see FIG. 8) (One-way ANOVA, $p=0.0006$). Additionally, vaccination with Pneumovax 23 also significantly reduced atherosclerotic lesions in the complete aorta, the aortic arch, the thoraco-abdominal aorta, as well as the iliac arteries (FIG. 9B). Indeed, as shown in FIG. 9B, the controls (right) had a much higher incidence of atherosclerosis as compared to the Pneumovax 23-treated animals (left). Furthermore, FIG. 10 illustrates the IgM reactivity in aortic roots of control (subpart a of FIG. 10) as compared to the Pneumovax 23-vaccinated mice (subpart b of FIG. 10) (magnification ×5). The photomicrographs from the IgM-reacted control (subpart c of FIG. 10) and pneumovax 23-vaccinated (subpart d of FIG. 10) mouse hearts clearly evidence intense IgM reactivity in the vaccinated samples as compared to the controls (magnification ×640). These findings likewise support that IgM antibodies act as atheroprotectans because Pneumovax 23-vaccinated mice had significantly more aortic and heart microvascular IgM than control mice (FIG. 10). Furthermore, because previous demonstrations evidenced that a hypercoagulable microvasculature in a rat heart transplantation is associated with CAV, this supports the idea that microvascular changes found in humans can be reproduced in rodents.

The role of innate immunity in the prevention or inhibition of CAV and graft failure represents a promising avenue for investigation. Because innate immunity plays a crucial role in the prevention or inhibition of atherosclerosis, it is worth a closer look at the specific role IgM NAbs plays in preventing or delaying the development of CAV and graft failure following heart transplantation. Based at least in part on the studies described herein, the data suggests that higher IgM antibody tissue and serum levels as well as IgM anti-PC serum levels are associated with beneficial outcomes (i.e. reduced CAV and prolonged graft survival) and that IgM antibodies may play a protective role in transplanted human heart patients.

As previously noted, MΦs were found to be reactive with IgM reactive capillaries, suggesting that arginase-1 can be used to evaluate the relationship with IgM anti-PC levels (see FIGS. 4A-4B). The possibility of IgM being an anti-PC antibody is also supported by data resulting from additional studies of the present disclosure focused on if IgM can be removed from heart biopsies by PC and CRP. Specifically, it was found that incubation of the biopsies with PC or CRP, but not other proteins like albumin (not shown) or the buffer control, removed IgM from the biopsies (FIG. 11). This IgM biopsy removal was also confirmed immunohistochemically (FIG. 12). FIG. 12 illustrates the results of displacement experiments: Subpart A of FIG. 12 shows a presence of vascular IgM following incubation with human albumin; subpart B of FIG. 12 is indicative of the removal of IgM with CRP; and subpart c of FIG. 12 shows the removal of IgM with PC (vascular IgM is denoted by orange reactivity (colocalization of green IgM and red endothelium) and the absence of IgM shows red only reactivity of endothelium.) Finally, ELISA studies of eluates showed IgM anti-PC with CRP (60.49±18.26 U/ml) and PC (56.67±19.96 U/ml) but not human albumin (0.0±0.0 U/ml) incubation.

Effect of NAbs on Macrophage Phenotypic Polarization In Vitro

Conventionally, it is known that IgM enhances MΦ phagocytosis, that phagocytosis induces MΦ activation, and that the nature of the activation determines a pro-inflammatory or anti-inflammatory response. However, to date, the specific mechanism(s) through which this process occurs has not been determined. Nevertheless, by examining the nature of MΦ activation after exposure to sera from mice previously immunized with a PC vaccine, it was possible to evaluate the ability of IgM to enhance MΦ phagocytosis. Using such a methodology, it has been determined that PC immunization induces production of specific IgM anti-PC NAbs and that these NAbs enhance MΦ phagocytosis of apoptotic cells and induce MΦ alternative (M2 anti-inflammatory) activation in vitro. Using the specific methodologies set forth herein, the ability of IgM to enhance MΦ phagocytosis was evaluated, as were the mechanisms responsible for the MΦ activation and the prolonged heart graft survival by PC immunization.

Two in vitro studies were used to examine the mechanisms responsible for the theory that anti-PC immunization prolongs heart graft survival. The first set of experiments test the effect of IgM anti-PC NAbs on phagocytosis activity. In the second set of experiments, the effect of sera from mice previously immunized with a PC vaccine was tested to determine the phenotype of the induced polarized MΦ. Accordingly, the effect(s) of anti-PC IgM NAbs were observed to elucidate the mechanism underlying the protective effect of IgM NAbs (namely, their affect on MΦ differentiation) by determining if PC-vaccinated C57BL/6 mice sera induce M2 MΦs.

Production of Sera.

For the anti-PC IgM NAbs studies on MΦ phagocytosis and polarization, randomly allocated mice (n=80) in experimental groups (n=20 each; Table 1) were subjected to experimental conditions as illustrated in Table 1, including 2 groups: group 1—mice able to produce IgG and IgM; group 2—IgM-deficient mice only able to produce only IgG.

TABLE 1

| Vaccination | Group 1 C57BL/6 (IgG + IgM producers) | Group 2 B6; 129S4-Ighm$^{tm1Che}$/J (IgM-deficient) |
|---|---|---|
| Experimental (PC-KLH) | N = 20 | N = 20 |
| Control (KLH) | N = 20 | N = 20 |

In group 1, normal C57BL/6 mice (IgG+IgM producers) were immunized by PC-keyhole limpet hemocyanin (PC-KLH) to induce anti-PC NAb production. In group 2, IgM-deficient mice that have impaired IgM antibody production, but still have an IgG response were immunized.

As controls for PC immunization, mice of the same genotypes were vaccinated with KLH. These procedures define the conditions of a 2×2 factorial design, as depicted in Table 1, with 2 immunization conditions (PC or KLH), and 2 mouse genotypes (normal C57BL/6 and IgM-deficient). Eight weeks after immunization, all mice were euthanized by $CO_2$ inhalation. Mouse sera from these animals was subsequently used to conduct the two in vitro studies. Additionally, the mouse serum IgM-anti-PC was analyzed using custom ELISA. Specifically, to establish the inflammatory milieu in the mouse sera used for the in vitro experiments, the sera was analyzed for pro-inflammatory TNF-α, IFN-γ, IL-1β, IL-6, IL-12 and anti-inflammatory IL-10 IL-4, IL-13, and TGF-β cytokines (SearchLight Multiplex Assay System, Aushom Biosystems).

In-Vitro Experiment #1: Effect of Anti-PC on MΦ Phagocytosis

To study the contribution of IgM to phagocytosis efficacy, aliquots of mouse sera from immunized mice were used to opsonize apoptotic cells employed to treat cultured MΦs.

Purification of Serum Anti-PC IgM.

IgM was purified from pooled mouse sera with ImmunoPure IgM Purification Kit (Thermo Scientific). IgM anti-PC was obtained after passing total IgM over PC-Sepharose columns (ADI, San Antonio, Tex.). The columns were washed with Phosphate Buffered Saline (PBS) pH 7.4 with Tween20 to remove non-bound IgM. These non-anti-PC antibodies were collected to use as controls (flow through immunoglobulins) in subsequent experiments. Bound PC-specific antibodies were eluted with 0.01M acetic acid and concentrated/buffer exchanged to PBS pH 7.4 using Centricon Plus-70 centrifugation filter units (Millipore, Billerica Mass., USA). Final IgM and IgM anti-PC concentrations were determined by IgM and IgM anti-PC ELISA respectively (ADI). IgM purity was confirmed by a single 85 kDa band on 8% reducing electrophorestic gel after staining with Coomassie blue. Western blot analysis confirmed the presence of IgM.

L-a-Lysophosphatidylcholine (LPC) Incubation and Apoptosis Evaluation.

Murine endothelial cells (MECs) derived from heart and lungs of wild-type C57BL/6 mice were cultured in a 96-well plate at 80% confluency and incubated with LPC (Sigma, 50-100 μM) for 16 hours to induce apoptosis. MEC apoptosis was detected with annexin V-FITC Apoptosis Detection Kit (Molecular Probes). Cells were resuspended and stained with annexin V-Fluorescein isothyocyanate and propidium iodide for 15 minutes at room temperature in the dark. Cell samples were analyzed by flow cytometry prior to adding the apoptotic cell suspension to the MΦs.

Opsonization of Apoptotic Cells.

To study the effects of mouse IgM anti-PC upon MΦ opsonization of apoptotic cells, a solution of LPC-incubated apoptotic cells ($\pm 0.5 \times 10^5$/mL) previously washed (twice in 500 μL PBS) was incubated with purified anti-PC IgM from mouse sera (10 μL) from all experimental groups previously described for 60 minutes at room temperature and wash (PC-KLH-vaccinated IgM-producers and IgM-deficient mice, KLH-vaccinated controls as well as total IgM or flowthrough IgM obtained from purified IgM [ADI] as positive and negative controls, respectively). To confirm the presence of IgM in the serum samples, the samples were incubated with a PE-labeled, F(ab')2 Fragment Goat Anti-Mouse IgM, 11 chain specific antibody (Jackson ImmunoResearch, Inc). The suspension was then washed 4 times with PBS (500 μL) prior to initiation of the phagocytosis assay.

MΦ Culture and Phagocytosis Assay.

Murine MΦs from spleen and the intraperitoneal cavity of wild-type C57BL/6 mice were suspended in complete culture media with 20% L929-conditioned medium (source of CSF-1) and seeded at $0.8 \times 10^6$/well in 6-well Lab-Tek chamber slides. After 2 hrs incubation at 37° C. in a 5% $CO_2$ incubator, non-adherent cells were removed and adherent cells were incubated in Dulbecco's Modified Eagle's Medium (DMEM) 10% FCS+20% L929 medium for 24 hrs. Thereafter, the cells were cultured for 12 without FCS and, before the phagocytosis assay was initiated, washed.

A suspension of serum opsonized apoptotic cells (30 μL) from each study group outlined in Table 1 was added to each well. MΦs were then incubated at 37° C. for 30 minutes for particle internalization. Phagocytosis was arrested on ice and the cells were washed twice with cold DMEM to remove the opsonized-APCs not associated with the MΦs.

To identify opsonized-APCs, a rabbit anti mouse caspase-3 antibody (Ab 13847) was added. Thereafter, 30 μL of (0.3 mg/mL, stock) Allophycocyanin (APC) fluorophore-conjugated anti-rabbit IgG was added to 500 μL PBS per well, overlaying the slide for 7 min. in the cold. The anti-rabbit impermeant fluorophore-conjugated antibody distinguishes between internalized particles and cell membrane-adherent particles failing to be engulfed, since the impermeant fluorophore-conjugated antibody exclusively stains external (exposed) apoptotic endothelial cells. Thus, external apoptotic cells were double-labeled and internalized particles single labeled. (The internalized cells were single labeled with PE rat anti-mouse IgM added to the serum.)

Additionally, MΦ nuclei were stained with nuclear dye Hoechst 33342/PI (8 μg/mL). The nucleoli of living cells showed low blue fluorescence, and apoptotic cells showed a higher level of blue fluorescence due to their condensed chromatin.

Determination of Phagocytic Index.

Phagocytosis efficacy is expressed in terms of the phagocytic index (PI), defined as: PI=(Number of total particles—Number of external particles/Number of total particles)× 100=Percentage of MΦ internalized particles per treatment. To determine the PI, images were captured with a Spot RT Color camera model #2.2.1 (Diagnostic Instruments) mounted to a Leica microscope (DMR, Nushbaum Inc., McHenry, Ill.), using Spot Advance Software version 4.7. Quantification was performed in digital images using Image-Pro Plus software Media Cybernetics (version 5.1.0.20). Furthermore, use of an automated KineticScan HCS reader allowed for the incorporation of time within this model as an additional dimension. The PI was used to evaluate the ability of each treatment to enhance MΦ phagocytosis.

In-Vitro Experiment #2: Effect of Anti-PC on MΦ Polarization/Activation

To evaluate the potential of anti-PC immunization upon M2 MΦ polarization towards an M2 anti-inflammatory phenotype, a similar experimental design as compared to the first study outlined herein was employed (see Table 1). Specifically MΦs were cultured, treated with serum from all immunized mice groups, and subsequently classified into known phenotypes through analysis of their specific markers.

MΦ Polarization.

Spleen and intraperitoneal murine MΦs were suspended in complete endotoxin-free DMEM supplemented with heat-inactivated 10% FCS and 20% L929-conditioned medium (source of studies CSF-1) and seeded at $0.8 \times 10^6$/well in 6-well tissue culture plates. After 2 hrs incubation at 37° C. in 5% $CO_2$, non-adherent cells were removed, and adherent cells were incubated in complete DMEM 10% FCS+20% L929-conditioned medium for 24 hrs. Cells were cultured for 12 hrs without FCS.

The MΦs were washed and sera (50 μg/mL) from each experimental group previously described were added to each well. NOS2, CD11c and Arg-2 were used to identify M1 MΦ and Arg-1 and CD206 were used to identify M2 MΦ. Furthermore, nitrite ($NO_2^-$) accumulation was measured and used as an indicator of NO production in MΦ culture supernatants (the vast majority of NO is converted to $NO_2^-$ in culture). The amount of nitrite measured was then quantified with the Griess reaction.

Thereafter, arginase activity was measured in MΦ lysates to determine the nature of the MΦ activation (the relationship between arginine metabolism and MΦ activation discussed above; see FIG. 1). To analyze enzyme activity, exogenous L-arginine was added to cell lysates and urea turnover was measured. Additionally, to differentiate among different M2 phenotypes, cytokine and chemokine secretion and expression were analyzed. Cytokines (e.g., TNF-α, IFN-γ, IL-1β, IL-6, IL12, IL-23, IL-10, IL-4, IL-13, IL-1ra and TGF-β) in cell supernatants were determined using SearchLight Multiplex Assays (Aushom Biosystems). Additionally, soluble chemokines were also quantified using ELISA, and insoluble chemokines were quantified by extracting cell RNA for RT-PCR, with real time quantitative PCR and northern blot analysis used to evaluate gene expression.

NF-κB Activation.

LPC-induced NF-κB activation and the possible inhibition of NF-κB activation by IgM anti-PC NAbs was detected by measuring the nuclear translocation of the NF-κB components p65 and p50 using GEMSA. MECs were treated for 24 hours with LPC either by itself, together with purified anti-PC IgM, total IgM or flow through IgM. Nuclear extracts were prepared as described. GEMSA was performed with $^{32}$P-labeled NF-κB as described. Oligonucleotide probes containing consensus sequences for NF-κB were purchased from Promega (Madison, Wis.). Supershift analyses were performed with NF-κB p50 antibodies (Upstate Biotechnology). Express of the IκBα (inhibitor κBα) was determined in the extracts (25 μg) by Western blot.

Statistical Analysis.

A two-way ANOVA was used to test the vaccination effect on mouse genotypes, as were Bonferroni post hoc tests to evaluate the differences between the test groups. Differences were considered statistically significant if P<0.05.

The results of the aforementioned in vitro experiments supported that PC immunization induced the production of specific IgM anti-PC NAbs. Furthermore, and importantly, the results were consistent with the theory that such NAbs enhance MΦ phagocytosis of apoptotic cells and induce MΦ alternative (M2 anti-inflammatory) activation in vitro.

Atheroprotective Effect of PC Vaccination in an In Vivo Mouse Heart Transplant Model.

In addition to the mechanisms underlying MΦ differentiation and the effect of NAbs thereon, it is also important to identify what artheroprotective effect (if any) a PC vaccination may have in vivo. In an attempt to determine if experimental induction of IgM anti-PC NAbs have a beneficial effect on graft rejection and survival, experiments were conducted in an in vivo heart transplant model to measure such antibodies' affect on CAV and graft survival. Specifically, heart transplants and experimental vaccination were performed in normal mice (C57BL/6) and in IgM-deficient mice. Thereafter, IgM antibody response was measured, and a determination made as to what (if any) effect the vaccination had on graft survival.

The study used a 2×3 factorial design to test the (a) main effect of immunization defined by 3 conditions: experimental vaccination vs. negative control (vaccination with KLH vehicle) vs. positive control (intra-peritoneal mouse polyclonal IgM); and (b) main effect of mouse genotype—normal C57BL/6 vs. IgM-deficient mice—on cardiac graft rejection (see Table 2). A total of 120 animals were randomly allocated in equal numbers (n=20 per group) to 1 of 6 experimental conditions as illustrated in Table 2. These sample sizes allow for the detection a 40% difference in cardiac graft rejection at a 0.05 significance with 80% power.

The experimental vaccine was designed to stimulate production of anti-PC IgM, thereby inducing M2 anti-inflammatory MΦ polarization, and ultimately reduce CAV and prolong graft survival (FIG. 13). Because it has previously been shown that passive immunization of anti-PC IgM via intra-peritoneal injections reduces vein graft lesion size in mice, and polyclonal IgM treatment reduces atherosclerosis in hypercholesterolemic apoE-deficient mice, it was expected that the positive control group would experience an effect on CAV and graft survival similar to that observed in the experimental vaccine group as anti-PC IgM was made available to this group directly via intra-peritoneal injections. The inclusion of knockout mice served as added controls, verifying that vaccination is only effective in animals that can genetically mount an IgM response.

TABLE 2

Experimental Design

| Treatment | Group 1 C57BL/6J (IgM + IgG producers) | Group 2 B6; 129S4-Ighm$^{tm1Che}$/J (IgM-deficient) |
|---|---|---|
| Experimental (PC-KLH) | N = 20 | N = 20 |
| Positive Control (Mouse polyclonal IgM) | N = 20 | N = 20 |
| Negative Control (KLH) | N = 20 | N = 20 |

Anti-PC Immunization and Experimental Design.

Eight-week-old mice with a C57BL/6 background (N=120) fed a normal Purina chow diet were used. Furthermore, an established major histocompatibility complex (MHC) class II-mismatched mouse model of CAV was used that involves a heterotopic, revascularized heart transplant from B6.C.H-2-bm12 (bm12, Jackson 001162) into a wild-type C57BL/6J (B6, H-2b, Jackson 000664)(IgG+IgM producers); and into B6; 129S4-Ighm$^{tm1Che}$/J (IgM-deficient, Jackson 003751) mice. Bm12 mice are a variant strain of C57BL/6 mice, in which a spontaneous mutation has occurred in the I-Ab locus, designated I-Abm12.

In this single MHC class II mismatch model, the majority of bm12 cardiac allografts survive up to 100 days and develop significant CAV, notable for intraluminal accumulation of mononuclear leukocytes (at 4 weeks post-transplant), intimal lesions (by 8 weeks), and accumulation of smooth muscle cells signifying fibroproliferative arteriosclerotic lesions (by 12 weeks). The limited alloreactive T-cell activation and emergence of a population of regulatory T-cells allow for long-term allograft survival with development of significant CAV.

The experimental groups were vaccinated with PC-KLH to enhance an anti-PC response, and the controls received mouse polyclonal IgM (positive control) or KLH vaccination (negative control). Vaccinations were done in 8 week-old mice with booster vaccinations every 2 weeks thereafter for the study duration. The positive control mice received intra-peritoneal injections of serum-derived mouse polyclonal IgM (Poly-IgM, Rockland) at a dose of 0.4 mg/mouse weekly until euthanasia.

Heart Transplant Studies.

All mice underwent heart transplantation at 16 weeks of age, 8 weeks after initial vaccination. Heterotopic heart transplantation was performed using a modification of Corry et al., as is known in the art. Specifically, the aorta and pulmonary artery of the donor hearts were anastomosed to the recipient's abdominal aorta and inferior vena cava, respectively, using a microsurgical technique. Ischemic time during the procedure was ~25 min, with a success rate of ~90%. Cardiac allograft viability was thereafter assessed by daily abdominal palpation. Graft failure was defined as heartbeat cessation and verified by autopsy. Loss of graft function within 48 hours of transplant was considered a technical failure (<10% on average).

Graft survival curves were calculated in accordance with the Kaplan-Meier method. Two-way ANOVA was used to test both the significance of the vaccination effect and the 2 different mouse genotypes on the percentage of arterial intimal lesion within the graft. Bonferroni post hoc tests were also used to evaluate differences among groups, which will be considered statistically significant if P<0.05.

Immunohistochemistry and Histopathology.

Heart transplants from all groups were evaluated for the presence of IgM antibodies (1B4B1, Southern Biotech) after PC vaccination. The presence of apoptotic cells was evaluated with antibody to caspase-3 (ab13847, abcam). Cellular infiltrates in heart transplants were studied with antibodies to MΦ (MOMA-2, Serotec), CD4 (BioLegend), and CD8 T lymphocytes (BD Biosciences). M1 MΦ were identified with antibodies to NOS2 (ab3523, abcam), CD11c (Santa Cruz, sc-28671) and Arg-2 (sc-20151, Santa Cruz); M2 MΦ were identified with antibodies to CD206 (Santa Cruz, sc-58987) and Arg-1 (Santa Cruz, sc-20150). Intermediate M1/M2 MΦs were identified by co-expression of CD11c and CD206. Proinflammatory cytokines IFN-γ (BD Pharminogen), TNFα (SouthernBiotech), IL-12 and IL-6, and anti-inflammatory cytokines IL-10 (BD Pharminogen), IL-4, IL-13, and TGFβ were studied to identify an association with M1 and M2 MΦs, respectively. Immunohistochemistry and histology were performed in all groups to evaluate any vascular/microvascular changes between experimental and control groups.

Flow Cytometry.

At the time of harvesting, to evaluate the spleen cell composition in response to vaccination and to identify the proportion of IgM-producing B-1 cells from other B-cell subpopulations, splenocytes were prepared and resuspended in a staining buffer containing PBS and 1% BSA. After blocking with an anti-Fc-γ receptor monoclonal antibody for 15 minutes at 4° C., $10^6$ cells were stained with antibodies specific for various surface markers [PerCP-anti CD19; PE-anti-mouse CD43, FITC-anti-mouse IgM (II/41)] or APC-anti-mouse CD21 in 100 μL staining buffer for 30 minutes at 4° C. More than $0.5 \times 10^5$ cells were analyzed. Splenic B-1 cells were identified as $CD19^+/IgM^+/CD43^+$, marginal zone (MZ) B cells as $CD19^+/CD21^+/CD23^-$, and follicular cells as $CD19^+/CD21^-/CD23^+$. MiniMACS Separator (MiltenyiBiotec Inc. 95602 Auburn, Calif., USA) was used for separation of CD19±cells. Cells were analyzed with a flow cytometer (FACScalibur, BD, USA).

ELISA.

Total amounts of IgM and specific antibodies to PC and KLH were quantified in blood samples obtained upon completion of the study, using customized enzyme-linked immunosorbent assay (ELISA) (ADI, San Antonio, Tex.). For determination of specific antibodies, PC-BSA (2 μg/mL), and KLH (10 μg/mL) were coated onto ELISA plate wells at a concentration of 2 μg/mL. Total and anti-PC IgM antibodies were revealed using anti-mouse IgM (BD Biosciences) alkaline phosphatase-conjugated secondary antibodies and p-nitrophenyl phosphate disodium salt substrate. Plates were read at 450 nm and data was read in duplicates; intra- and interassay variability was calculated.

Serum Cytokine and Immunoglobulin Analysis.

IgM pro-(INF-γ, TNF-α, IL-1β, IL-12) and anti-inflammatory (IL-10, IL-4, IL13, TGF-β) cytokine levels were measured in blood obtained upon at harvesting with the SearchLight Multiplex Assay (Aushon Biosystems). All data was then compared to established tissue and flow cytometry data to identify the predominant pattern response in mice with or without an IgM response.

In accordance with the present application's previous disclosure that investigations in humans showed that the presence of microvascular IgM antibodies is associated with enhanced allograft survival, the results of the foregoing in vivo experiment support that experimental induction of IgM NAbs with PC vaccination have a positive effect on graft survival in a mouse model of heart transplantation (i.e. prolong graft survival). Indeed, the negative control group (KLH vaccination (no active PC antigen)) experienced a significantly greater incidence of CAV and shorter graft survival times, thereby indicating an association between lack of IgM response in PC-vaccinated mice and more rapid cardiac-graft rejection. Accordingly, it is probable that the protective IgM antibodies are directed against PC, which is exposed in microvascular apoptotic cells. The present disclosure supports that PC immunization leads to an enhanced NAb response that confers graft protection by enhancing the microvascular apoptotic cell clearance.

The Role of NAbs on Atheroprotection and Macrophage Polarization in Transplant Patients.

Now that the role of IgM anti-PC in protecting tissue allografts against chronic rejection through their effects on MΦ differentiation or polarization and endothelial cell activation has been verified in vitro and in vivo in murine models, it is important to verify that such data successfully translates to human heart transplant patients. In furtherance of this, experiments were conducted to define the relationship between anti-PC Nab serum levels (high levels—e.g., more than about 20 units/ml—are associated with reduced vein graft plaque in mice and reduced atherosclerosis in mice and humans) and the development of CAV, graft failure, and/or major adverse cardiac events in human heart transplant patients. Furthermore, to gather support for a possible mechanistic interpretation, experiments were devised to determine if a positive correlation exists between high IgM anti-PC levels, high cardiac microvascular IgM, and a reduced incidence of inflammation and coagulation activation in transplanted hearts, since increased inflammation and coagulation are known to be early markers of CAV and graft failure. Additionally, it was investigated as to whether patients with lower levels of inflammation have more abundant M2 anti-inflammatory MΦs and if purified human IgM anti-PC induces M2 MΦ differentiation in vitro.

In sum, the following aspects were evaluated: (a) the ratio of IgM NAbs to PC in heart transplant patients; (b) the relationship between IgM anti-PC levels and the subsequent development and progression of CAV, major cardiac events (MACE) associated with CAV, and the development of graft failure; (c) the relationship between IgM anti-PC and IgM antibodies in graft microvasculature; (d) the relationship among IgM anti-PC levels, serum CRP levels, and microvascular endothelial activation; and (e) the relationship between IgM anti-PC in serum, IgM antibodies within the graft microvasculature, and the presence of prothrombotic changes in the cardiac microvessels.

Human biopsy samples from a cohort of heart transplant patients (n=445) were prospectively obtained serially between 10 days and 18 years post-transplant in each of those patients (13 per patient) to perform all proposed studies. IgM antibodies within transplanted heart tissues were evaluated with immunohistochemistry in frozen sections and endothelial localization was visualized with double-staining technique using *Ulex Europaeus* lectin.

Serum IgM anti-PC NAbs was evaluated using ELISA (ADI, San Antonio, Tex.). To confirm that IgM within the heart microvessels is directed to PC, the antibodies were eluted from the heart tissue samples and measured the eluates in specific ELISAs (ADI, San Antonio, Tex.). The presence of increased inflammation was determined immunohistochemically with antibodies to CRP and ICAM-1. Reduced thrombosis was identified using antibodies to fibrin, antithrombin, and tissue plasminogen activator. MΦ phenotypes were also assessed with 4-color immunohistochemistry and M1 and M2 MΦs characterized with antibodies to TNF/IL-1/CCR2/IL-12/23 and CD163/IL-10/CD206, respectively.

Logistic regression was employed to model the prognostic value of IgM anti-PC NAbs (measured during the entire follow-up) to predict 10-year CAV and graft failure, as well as CAV progression. Statistical models were cross-validated on 200 bootstrap samples drawn with replacement from the original patient sample. The Youden Index calculated on receiver operator characteristic (ROC) curves identified optimum cut points for prediction, and model sensitivity, specificity, and predictive accuracy were investigated. Model discrimination was evaluated by calculating the area under the ROC curve.

Biopsy Samples:

The human serial endomyocardial heart biopsy samples were obtained from a local biorepository, where such samples were stored at −80° C. The samples were collected over a period of time from 445 patients during their entire post-transplant period at all routine follow-up visits. The inclusion of serial biopsies obtained between 10 days and 18 years post-transplant in each of those patients (13 total biopsies per patient) allowed for the completion of all proposed studies.

Determination of Antibody Levels and Binding Specificities.

IgM anti-PC antibodies were measured with ELISA (Athera CVDefine™ kit, Athera Biotechnologies AB, Stockholm, Sweden). The kit was based on PC covalently linked to bovine serum albumin (PC-BSA) coated onto 96-well Nunc Maxisorp micro-titer plates and the assay was carried out pursuant to the manufacturer's recommendations. All readings of results were performed on ELISA Multiscan Plus spectrophotometer (Molecular Devices Emax, San Francisco, Calif.). The binding specificity of the human anti-PC IgM was determined in a competitive ELISA with PC hapten. Briefly, hapten was mixed with affinity-purified anti-PC from pooled IgM and incubated on CVDefine plates. Antibody was detected with a specific secondary antibody.

Studies to Demonstrate IgM Anti-PC in Heart Biopsies:

IgM from heart biopsies was removed using PC (50 mM), CRP (2.58 mg/ml) or albumin (1 mg/ml) concentrations proven to be effective in preliminary studies (see FIG. 11). To verify if the IgM removed from the heart biopsies is PC-specific, ELISA was performed.

Cell Studies:

Human aortic and/or microvascular endothelial cells were cultured in a 96-well plate at 80% confluency and incubated with LPC (Sigma, 50-100 μM) for 16 hours under conditions known to induce cell apoptosis. Cell apoptosis was detected using an annexin V-FITC Apoptosis Detection Kit (Molecular Probes). Cell samples were then analyzed by flow cytometer for apoptosis. The apoptotic cells were pretreated with anti-PC IgM to determine if their pre-opsonization favored M2 MΦ polarization. Apoptotic cells were pretreated with IgM anti-PC, purified from the patient's sera (available from the biorepository) or with purified human IgM (total IgM, IgM anti-PC, non-anti-PC IgM [flow through immunoglobulins] or none). Human MΦs were then cultured and treated with the pre-opsonized apoptotic cells or with non-opsonized controls. Thereafter, the MΦs were analyzed for specific markers to classify them into known phenotypes. MΦ phenotypes were also assessed using flow cytometry, characterizing M1 MΦs with antibodies to TNF/IL-1/CCR2/IL-12/23, and M2 polarized MΦs with antibodies to CD163/IL-10/CD206 in human cells. Intermediate M1/M2 MΦs were identified by co-expression of CD11c and CD206. Human aortic and/or microvascular endothelial cells treated with LPC either by itself, together with purified anti-PC IgM, total IgM or flowthrough IgM, and nuclear extracts were prepared (as described for the studies on the effect of NAb on macrophage phenotypic polarization and endothelial activation in vitro previously discussed herein) to determine NFκB nuclear expression by GEMSA. IκBα expression was determined in cell extracts by Western blot analysis and RNA was isolated by the guanidinium isothiocyanate/CsCl ultracentrifugation method and subsequently subjected to Northern analysis for ICAM-1 expression.

Data and Statistical Analysis:

The primary (dichotomous) outcome was CAV-associated graft failure, which was coded: 1=present; 0=absent. Secondary outcomes were time to CAV-associated graft failure and number of MACE. Standard descriptive statistics were used to summarize the data. Univariate associations between demographic, clinical, and laboratory variables and the outcome was also summarized with parametric or nonparametric tests. Variables found to be associated with outcome were considered as confounding variables in multivariable statistical models. Consistent with past experience using this type of model, significant confounding variables likely included recipient sex and race, number of HLA-AB mismatches, number of 2R-3R rejection episodes, and immunosuppressive regimen used (cyclosporine [Cya] or tacrolimus [Tac] plus azathioprine [AZA] versus Cya or Tac plus mycophenolate mofetil).

Stepwise logistic (and log-binomial) regression with backward elimination was used to determine if IgM anti-PC levels were independently predictive of CAV-associated graft failure. Model cross validation was accomplished using a variation of Efron's bootstrap methodology. Models were estimated on 200 bootstrapped samples drawn with replacement from the study sample. Predictor variables retained at a significance level of $P \leq 0.05$ in $\geq 60\%$ of the bootstrapped models was included in the final model. The Youden Index calculated from receiver operating characteristic (ROC) curves was used to identify optimum cut-off values for predicted probabilities. Sensitivity, specificity, positive and negative predictive accuracy were calculated to summarize model performance. The C-statistic (area under the ROC curve) was calculated as an indicator of the model's discriminative accuracy. Model coefficients and risk ratios (RRs) were also reported. Cox proportional hazard regression was employed to model the effect of IgM anti-PC on time to CAV-associated graft rejection, controlling for the additional clinical and laboratory variables also found to be associated with the outcome. To determine whether NAb anti-PC serum levels are predictive of the MACE associated with CAV, we employed a negative binomial regression model. Finally, because patients in the sample had different follow-up times, we included time as an offset variable in the model. Model coefficients and incidence rate ratios were reported.

Interestingly, the presence of high levels of a specific IgM anti-PC NAb in the serum of human heart transplant recipients were associated with increased microvascular myocardial IgM/IgG, an increased number of M2 MΦs, and reduced signs of inflammation and thrombosis. Conversely, patients with reduced IgM/IgG anti-PC antibodies (e.g., less than about 20 units/ml serum) exhibited signs of inflammation, an increased number of M1 MΦs, and prothrombotic and activated graft microvasculature, which has previously been linked to an increased incidence of CAV and graft failure. Finally, serum IgM anti-PC as well as IgM anti-PC obtained from purified human IgM or IgG (ADI, San Antonio, Tex.), induced alternative (M2 anti-inflammatory) MΦ polarization in vitro in humans.

In light of the information and new data disclosed herein, vaccines and methods of the present disclosure, and relating to applications thereof, will now be discussed. In at least one exemplary method of reducing an incidence of transplant rejection, the method comprises the step of treating an individual who has or will receive transplanted tissue with at least one substance sufficient to increase innate immunity of the individual. Exemplary substances used may depend on the type of treatment (also referred to herein as "immunization") desired by the treating physician and/or patient. The transplant can be heart or heart tissue, as generally referenced herein, or other organs, such as, but not limited to, kidney, lung, liver, intestines, and pancreas or any organ with a vascular system, including placenta which is also considered a transplant, in said tissue. Exemplary substances may include, but are not limited to, PC, IgM anti-PC and/or IgG anti-PC, and can be used to treat and/or prevent (in the case of exemplary vaccines of the present disclosure) the various conditions referenced herein or that otherwise result from organ and/or tissue transplantation. In various embodiments, substances and/or vaccines may be used so to administer and/or ultimately result in IgM anti-PC levels of or between 50 and 100 units/mL, or more.

For example, and in at least one embodiment, an exemplary method comprises treating an individual with PC directly, which may, in certain embodiments, be referred to herein as PC conjugated to keyhole limpet hemocyanin (PC-KLH). Administration of such a substance results in an innate response by acting upon B1 cells to induce IgM anti-PC NAbs. The IgM anti-PC NAbs, consistent with the present disclosure, induce favorable M2 MΦ polarization to clear the transplanted organ of damaged cells, by way of oxidized low-density lipoproteins (oxLDLs) acting upon M2 MΦs to reduce incidences of CAV or chronic rejection of other solid organs. This mechanism ultimately reduces incidences of, reduces the risk of, and/or prevents CAV or chronic rejection, and is facilitated by the release of several byproducts from M2 MΦs including, but not limited to, interleukin-10 (IL-10), transforming growth factor-beta (TGF-β), and/or arginase-1.

Furthermore, in at least one alternative embodiment, an exemplary method comprises treating an individual with PC directly to induce high levels of a specific IgM/IgG anti-PC NAb in the serum of a human transplant recipient. As high levels of these antibodies in the serum is associated with increased microvascular myocardial IgM/IgG, this step also results in the inducement of favorable M2 MΦ polarization, thereby increasing the number of M2 MΦs and reducing signs of inflammation and thrombosis.

In at least one exemplary embodiment of the present disclosure, a composition is disclosed for preventing or treating chronic allograft rejection. In accordance with the previously described methods for treating an individual, the composition may be in the form of a vaccine, immunization or other treatment and comprises a therapeutically effective amount of PC sufficient to initiate the production of anti-PC natural antibodies following its administration to an allograft recipient (or soon to be recipient). Accordingly, upon administration of such composition and through the biological mechanisms described herein, the PC immunization induces the production of specific IgM and/or IgG anti-PC NAbs, which subsequently induces alternative (M2 anti-inflammatory) MΦ activation.

In at least another embodiment of a method of treating an individual, the present disclosure includes disclosure of treating the individual with IgM and/or IgG anti-PC directly. Administration of such a substance results in a direct IgM/IgG effect by causing apoptotic cells with a PC element to bind to M2 MΦs by way of IgM/IgG anti-PC, with said elements acting upon M2 MΦs to reduce incidences of CAV, inflammation, and/or chronic rejection. This mechanism to ultimately reduce incidences of, reduce the risk of, and/or prevent CAV, inflammation, or chronic rejection is also facilitated by the release of several byproducts from M2 MΦs including, but not limited to, IL-10, TGF-β, and/or arginase-1.

Said methods, as referenced herein, are performed to up-regulate the individual's innate immune response. Depending on the type of individual (characterized by transplant type and other risk factors), one method (leading to an innate immune response) versus another method (producing a direct IgM/IgG effect) may be preferred.

The feasibility of these approaches (different methods of treating and/or preventing incidences of transplant rejection) are supported by previous demonstrations that both active immunization with PC (which stimulates the production of IgM anti-PC and/or IgG anti-PC NAbs produced by B1 cells that induce favorable M2 MΦ polarization to clear the transplanted organ/tissue of damaged cells), as well as passive immunization, via direct infusion/injection of IgM anti-PC and/or IgG anti-PC, suppress the development and progression of atherosclerosis. Prior to the present disclosure, consideration of the same immunizations to reduce incidences of, reduce the risk of, or prevent the development of CAV or chronic rejection in connection with transplantation was not made because, as noted above, suppression of a transplant patient's immune response, as compared to the present disclosure to enhance the patient's immune response, has been the standard in the medical arts for many years. Furthermore, passive immunization with IgM anti-PC and/or IgG anti-PC has been shown to reduce inflammation and vein graft lesion size in mice, and ultimately result in increased microvascular myocardial IgM and/or IgG, an increased number of M2 MΦs and reduced signs of inflammation and thrombosis in human heart transplant recipients.

As referenced above, active immunization with PC is expected to stimulate production of specific IgM and/or IgG anti-PC NAbs, which would induce favorable M2 MΦ polarization, clearing the transplanted organ of damaged cells (the initiating source of CAV formation or development of chronic rejection) and ultimately prolonging graft survival. Alternatively, the same protective effect might be achieved via passive immunization by injecting IgM and/or IgG anti-PC directly. Boosting a NAb atheroprotective response interrupts the pro-inflammatory environment, both systemically and locally within the microvessels of the transplanted organ.

The present disclosure, as referenced above, challenges current paradigms and opens new avenues in transplantation treatment and research. Current research directed toward cellular and antibody-mediated mechanisms should be critically assessed by experiments designed to determine whether enhancing the recipient's innate NAb response protects the transplanted organ from chronic rejection.

In addition to the foregoing, exemplary method embodiments of the present disclosure can be performed to address the natural progression of atherosclerosis in the general population. As referenced above, it has been observed that the CAV in transplant patients very much resembles the natural progression of atherosclerosis in the general population (similar plaque morphology and composition), albeit substantially accelerated in transplant patients. The various methods of the present disclosure may also be used, along with the concept of vaccination as referenced herein for example, to target high risk patients, such as those patients who are diabetic, hypertensive, hyperlipidemic, and/or patients who smoke. In at least one embodiment, a method of the present disclosure, as referenced herein, can be performed to treat pre-eclampsia.

Exemplary diagnostic methods are also described herein. For example, in at least one embodiment, a non-invasive and accurate method for screening an allograft recipient for chronic allograft rejection or simply being at-risk for developing the same is disclosed. Such inventive method is extremely significant as the only options currently available for the early detection of patients at-risk of CAV are invasive, typically not initiated until at least one year post-transplantation, expensive, inaccurate and not comprehensive, and pose an increased risk to the patient.

In at least one exemplary embodiment, a method of screening an allograft recipient for chronic allograft rejection or being at-risk for developing the same is disclosed. As referenced above, high levels of serum NAbs are associated with a reduced incidence, or delayed onset, of chronic allograft rejection, which can be used as an effective biomarker in evaluating the status of a graft. Conversely, those patients lacking IgM-mediated atheroprotection show a pro-thrombotic microvasculature and are associated with an increased incidence of CAV and graft failure. Similarly, low serum levels of IgM/IgG anti-PC NAbs are associated with an increased incidence of CAV, graft failure, and major adverse cardiac events in human heart transplant recipients. Indeed, such patients exhibit signs of inflammation, an increased number of M1 MΦs, increased levels of serum CRP, reduced levels of natural antibodies within the graft itself, and a pro-thrombotic and activated graft microvasculature.

The novel method disclosed herein exploits the relationship between NAb levels and the onset of CAV, thus providing a powerful, accurate, and noninvasive method through which allograft recipients can be screened for the early detection of CAV or other chronic rejection. Specifically, the NAb levels may be measured in an allograft recipient to determine if they fall within the appropriate range (e.g., between about 20 U/ml to about 60 U/ml). If, for example, the measured levels of serum NAbs fall below the desired range, this is a strong indicator that the patient is at-risk for, or currently experiencing, the early stages of CAV or other chronic allograft rejection. As noted above, such indicative NAbs may comprise IgM, IgG, as well as the related anti-PC NAbs. Furthermore, such measurements may be taken from the patient's blood serum, tissue, biopsy of the allograft itself, and/or any other biological sample where such natural antibodies are expressed.

Other novel biomarkers may be similarly exploited for the early detection of CAV or other chronic allograft rejection. In at least one embodiment, the early diagnosis of CAV may be achieved by studying the downstream effects of NAb levels. For example, reduced IgM levels are significantly related to subsequent fibrin deposition within a heart. As such, fibrin deposits within graft microvasculature can be indicative of reduced NAb levels and, thus, the onset of chronic allograft rejection. Furthermore, because fibrin deposits are typically evidenced by increased serum cardiac troponin I levels, a lack of anticoagulant and fibrinolytic capacity, and up-regulation of endothelial ICAM-1, incidence of the same can be utilized as early biomarkers for negative allograft outcome. Accordingly, in at least one embodiment of the present disclosure, a diagnostic method comprises screening an allograft recipient for CAV simply by performing an analysis of the patient's blood and/or tissue biopsy sample. If such analysis detects elevated cardiac tropnin I levels and/or a lack of anticoagulant and fibrinolytic capacity, and up-regulation of ICAM-1 expression in endothelial cells, such results are indicative of the patient either being at-risk for developing, or currently experiencing early onset of CAV or chronic allograft rejection.

The diagnostic methods described herein are noninvasive, accurate and inexpensive to perform. Furthermore, due to the strong relationship between NAb serum levels and subsequent downstream events in allograft recipients, the results are highly accurate.

Additional Data

As noted above, cardiac allograft vasculopathy (CAV) is a serious complication in adult and pediatric heart transplantation. Several causes including inflammation and innate immunity have been proposed for CAV. The present disclosure supports the determination that immunoglobulin M (IgM) natural antibody (NAb) components of innate immunity are protective in CAV.

Methods

One hundred and seventy-two (172) adult heart transplant patients (having a number of serial biopsies per patient in first three months post-transplant) were followed for several years and subsequently analyzed. CAV was diagnosed with serial angiographies for each patient. The percentage of microvascular IgM was quantified with double staining (IgM/CD31 or *Ulex europaeus* lectin). IgM and IgM anti-phosphorylcholine (PC) from biopsy eluates were determined with immunoblotting and enzyme-linked immunosorbent assays (ELISAs). Statistical analyses used univariate logistic regression, multivariate stepwise models, and Kaplan-Meier curves for different tertile groups.

Results

Of the 172 patients analyzed, 67 had low IgM (<30% microvessels) in all biopsies, 64 had all biopsies with high IgM (>50% microvessels) and 41 showed oscillation of high and low IgM in their biopsies. Steady high microvascular IgM (>50%) had a significant atheroprotective effect at 1-year (z: $-3.24$; p<0.001), 5-year (z: $-4.75$; p<0.0001) and 10-year (z: $-3.29$; p<0.001) post-transplant compared with patients with steady low IgM (<30%). Patients with IgM oscillation had a mild atheroprotective effect only at 5-years (z: $-2.10$; p=0.04), but not at 1-year (z: $-1.82$; p=0.07) or 10-years (z: $-1.12$; p=0.3). When considering the first biopsy only (post-transplant), high IgM had significant atheroprotection at 1-year (z: $-3.52$; p<0.0001), 5-year (z: $-5.38$; p<0.0001) and 10-year (z: $-3.66$; p<0.0001), post-transplant.

To determine if biopsy-associated IgM was IgM anti PC, we demonstrated that (a) biopsy IgM can be removed by PC and C-reactive protein (CRP) but not albumin or control buffer; (b) western blots from eluates showed IgM following incubation with PC and CRP but not albumin or buffer; and (c) immunohistochemistry showed biopsy removal with PC and CRP but not albumin or buffer. Finally, ELISA studies of biopsy eluates showed IgM anti-PC with PC (56.7±20.0 U/ml) and CRP (60.5±18.3 U/ml), but not human albumin (0.0±0.0 U/ml) incubation.

Conclusions

In the studies referenced above, we successfully demonstrated that IgM anti-PC NAbs in heart transplant patients are atheroprotective. Results obtained from the first post-transplant biopsy suggest that high IgM anti-PC at transplantation is atheroprotective during follow-up. Our data, consistent with the disclosure contained within the present patent application, provides a basis for a fundamentally new approach to patient diagnosis and ultimately management using therapies designed to enhance the recipient's own IgM anti-PC NAb-mediated response.

Inflammation and Thrombosis

Inflammation and thrombosis are risk factors for CAV, MACE, and graft failure due to CAV (GFDCAV). We also performed analyses to determine if cardiac immunoglobulin M (IgM) antibodies, shown by us to be anti-phosphorylcholine (PC), are protective upon CAV severity, MACE, and GFDCAV adjusting for inflammation and thrombosis, to support the hypothesis that enhancing an IgM anti-PC specific response may be beneficial.

Methods

The 172 adult heart transplant patients previously referenced herein (having an average of 5.2±1.0 biopsies/patient) were followed 8.9±5.0 years and subsequently analyzed. CAV and CAV severity were evaluated with angiograms (5.3±1.0/patient). MACE included myocardial infarction, need for percutaneous coronary interventions and/or coronary artery bypass grafting, and cardiac death. Thrombosis (fibrin, antithrombin, tissue plasminogen activator [tPA]) and inflammation were studied with immunohistochemistry and/or ELISA. IgM percentage was obtained from double staining. Logistic regression adjusting for groups (IgM values) was used.

Results 67 patients had low IgM (<30% vessels) and 64 high IgM (>50% vessels) in all biopsies; the others showed IgM oscillation (IgMosc). For inflammation, thrombosis and IgM as risks for CAV, we found that: (a) C-reactive protein (CRP) was atherogenic (z: 1.95; p=0.05), and steady high IgM (z: $-2.84$; p=0.01) and IgMosc (z: $-2.28$; p=0.02) were atheroprotective at 1 year; (b) interleukin-6 (IL-6) was atherogenic (z: 1.95; p=0.05) and high IgM (z: $-3.8$; p<0.01) and IgMosc (z: $-2.0$; p=0.04) were atheroprotective at 5 years; and (c) high IgM was atheroprotective at 10 years (z: $-2.8$; p=0.01). Loss of tPA was a risk for severe CAV (z: 2.02; p=0.04), while IgMosc was protective against severe CAV (z: $-3.21$; p<0.01) at 5 years; and high IgM (z: $-2.47$; p=0.01) and IgMosc (z: $-3.08$; p<0.01) were protective against severe CAV at 10 years. Loss of tPA was a risk for MACE (z: 2.77; p=0.01), while high IgM (z: $-3.58$; p<0.01) and IgMosc (z: $-3.24$; p<0.01) were protective against MACE. Loss of tPA was associated with more GFDCAV (z: 2.00; p=0.04), while high IgM (z: $-2.90$; p<0.01) and IgMosc (z: $-2.71$; p=0.01) protected against GFDCAV.

Conclusions

In the aforementioned studies, we successfully determined that (a) IL-6, CRP, and loss of tPA were atherogenic; (b) loss of tPA was a risk for severe CAV, MACE and GFDCAV; and (c) high IgM (>50% vessels) and IgMosc protected against CAV, severe CAV, MACE and GFDCAV. Our data, consistent with the disclosure contained herein, suggest that enhancing an IgM anti-PC specific response may be beneficial, providing a fundamentally new approach regarding the same.

While various embodiments of methods for reducing incidences of, diagnosing and treatment transplant rejection and substances and vaccines to facilitate the same have been described in considerable detail herein, the embodiments are merely offered as non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the present disclosure. Indeed, this disclosure is not intended to be exhaustive or limiting with respect to the content thereof. The scope of the disclosure is to be defined by the appended claims, and by their equivalents.

Furthermore, in describing representative embodiments, the present disclosure may have presented a method and/or a process as a particular sequence of steps. However, to the extent that the method or process does not rely on the particular order of steps set forth therein, the method or process should not be limited to the particular sequence of steps described. As one of ordinary skill in the art would appreciate, other sequences of steps may be possible. Therefore, unless expressly stated otherwise, the particular order of the steps disclosed herein should not be construed as limitations of the present disclosure. In addition, any claims directed to a method and/or process should not be limited to the performance of their steps in the order written (unless expressly specified otherwise), and one skilled in the art can readily appreciate that the sequences may be varied and still remain within the scope of the present disclosure.

The invention claimed is:

1. A noninvasive method of screening a cardiac allograft recipient for being at-risk for developing cardiac allograft vasculopathy, the method comprising the steps of:
   withdrawing at least one biological sample from a cardiac allograft recipient; and
   analyzing the at least one biological sample for one or more biomarkers indicative of the presence of fibrin deposits within the cardiac allograft microvasculature;
   wherein detection of the one or more biomarkers indicates that the cardiac allograft recipient is at-risk for developing the fibrin deposits within the cardiac allograft vasculature indicative of cardiac allograft vasculopathy;
   wherein the one or more biomarkers is/are selected from the group consisting of an elevated level of cardiac troponin I, reduced anticoagulant and fibrinolytic capacities of the serum, detection of up-regulation of endothelial intercellular adhesion molecule-1 (ICAM-1) expression, and detection of an elevated nuclear factor-kappa B (NF-KB) nuclear expression; and
   wherein if the cardiac allograft recipient is at-risk of developing the fibrin deposits within the cardiac allograft vasculature indicative of cardiac allograft vasculopathy, the method further comprises the step of:
   administering a therapeutically effective amount of phosphorylcholine to the cardiac allograft recipient to treat and/or prevent cardiac allograft vasculopathy, which selectively enhances a natural antibody-mediated innate immune response in the cardiac allograft recipient by increasing levels of immunoglobulin M and/or immunoglobulin G anti-phosphorylcholine natural antibodies in an allograft recipient's serum.

2. The method of claim 1, wherein:
the step of withdrawing the at least one biological sample comprises withdrawing serum from the cardiac allograft recipient; and
at least one of the biomarkers is selected from the group comprising:
   an elevated level of cardiac troponin I in the serum as compared to a control serum sample, and
   detection of reduced anticoagulant and fibrinolytic capacities of the serum as compared to a control serum sample.

3. The method of claim 1, wherein:
the step of withdrawing the at least one biological sample comprises extracting a biopsy sample from the cardiac allograft recipient, the biopsy sample comprising endothelial cells; and
at least one of the biomarkers is selected from the group comprising:
   detection of up-regulation of endothelial intercellular adhesion molecule-1 (ICAM-1) expression in endothelial cells from the biopsy sample as compared to a control tissue sample, and
   detection of an elevated nuclear factor-kappa B (NF-KB) nuclear expression in the endothelial cells from the biopsy sample as compared to a control tissue sample.

4. The method of claim 1, wherein the step of administering a therapeutically effective amount of phosphorylcholine further comprises administering a vaccine to the allograft recipient, the vaccine comprising a composition for preventing or treating chronic allograft rejection; and
   wherein the therapeutically effective amount of phosphorylcholine is sufficient to initiate the production of anti-phosphorylcholine natural antibodies in a mammal following administration thereto.

5. The method of claim 4, wherein the vaccine is administered before detection of any chronic allograft rejection.

6. The method of claim 1, wherein the step of administering a therapeutically effective amount of phosphorylcholine results in the reduction or prevention of atherosclerosis in the allograft recipient.

7. The method of claim 1, wherein the step of administering a therapeutically effective amount of phosphorylcholine results in the reduction of risk factors in Cardiac Allograft Vasculopathy (CAV), Major Cardiac Events (MACE), and Graft Failure Due to CAV (GFDCAV).

8. The method of claim 1, wherein the increased levels of immunoglobulin M and/or immunoglobulin G anti-phosphorylcholine natural antibodies in the allograft recipient's serum induces alternative M2 anti-inflammatory macrophage polarization.

9. The method of claim 1, further comprising the step of clearing the allograft of damaged cells by way of inducing alternative M2 anti-inflammatory macrophage polarization.

10. A noninvasive method of diagnosing early onset of chronic allograft rejection, the method comprising the steps of:
   measuring an amount of a first natural anti-phosphorylcholine antibody within at least one biological sample from a cardiac allograft recipient;
   comparing the amount of the first anti-phosphorylcholine natural antibody in the biological sample with the amount of the first anti-phosphorylcholine natural antibody in a control sample;
   analyzing the at least one biological sample for one or more biomarkers indicative of the presence of fibrin deposits within the cardiac allograft microvasculature;
   wherein a decrease in the amount of the first anti-phosphorylcholine natural antibody in the sample from the cardiac allograft recipient as compared to the amount of the first anti-phosphorylcholine natural antibody in the control sample indicates a diagnosis of the allograft recipient being either at-risk for developing the fibrin deposits within the cardiac allograft vasculature indicative of chronic allograft rejection; and
   wherein detection of the one or more biomarkers in the at least one biological sample indicates that the cardiac allograft recipient is at-risk for or developing the fibrin deposits within the cardiac allograft vasculature indicative of cardiac allograft vasculopathy;
   wherein the one or more biomarkers is/are selected from the group consisting of an elevated level of cardiac troponin I, reduced anticoagulant and fibrinolytic capacities of the serum, detection of up-regulation of endothelial intercellular adhesion molecule-1 (ICAM-1) expression, and detection of an elevated nuclear factor-kappa B (NF-KB) nuclear expression; and
   wherein if the cardiac allograft recipient is at-risk of developing the fibrin deposits within the cardiac allograft vasculature indicative of cardiac allograft vasculopathy, the method further comprises the step of:
administering a therapeutically effective amount of phosphorylcholine to the cardiac allograft recipient to treat and/or prevent cardiac allograft vasculopathy, which selectively enhances a natural antibody-mediated innate immune response in the cardiac allograft recipient by increasing levels of immunoglobulin M and/or immunoglobulin G anti-phosphorylcholine natural antibodies in an allograft recipient's serum.

11. The method of claim 10, further comprising the step of withdrawing the at least one biological sample by withdrawing serum from the cardiac allograft recipient; and wherein
at least one of the biomarkers is selected from the group comprising:
an elevated level of cardiac troponin I in the serum as compared to a control serum sample, and
detection of reduced anticoagulant and fibrinolytic capacities of the serum as compared to a control serum sample.

12. The method of claim 10, further comprising the step of withdrawing the at least one biological sample, wherein withdrawing the at least one biological sample comprises extracting a biopsy sample from the cardiac allograft recipient, the biopsy sample comprising endothelial cells; and
at least one of the biomarkers is selected from the group comprising:
detection of up-regulation of endothelial intercellular adhesion molecule-1 (ICAM-1) expression in endothelial cells from the biopsy sample as compared to a control tissue sample, and
detection of an elevated nuclear factor-kappa B (NF-KB) nuclear expression in the endothelial cells from the biopsy sample as compared to a control tissue sample.

13. The method of claim 10, wherein the step of administering a therapeutically effective amount of phosphorylcholine further comprises administering a vaccine to the allograft recipient, the vaccine comprising a composition for preventing or treating chronic allograft rejection; and
wherein the therapeutically effective amount of phosphorylcholine is sufficient to initiate the production of anti-phosphorylcholine natural antibodies in a mammal following administration thereto.

14. The method of claim 10, wherein the step of administering a therapeutically effective amount of phosphorylcholine results in the reduction or prevention of atherosclerosis in the allograft recipient.

15. The method of claim 10, wherein the step of administering a therapeutically effective amount of phosphorylcholine results in the reduction of risk factors in Cardiac Allograft Vasculopathy (CAV), Major Cardiac Events (MACE), and Graft Failure Due to CAV (GFDCAV).

16. The method of claim 10, wherein the increased levels of immunoglobulin M and/or immunoglobulin G anti-phosphorylcholine natural antibodies in the allograft recipient's serum induces alternative M2 anti-inflammatory macrophage polarization.

17. A noninvasive method of screening a cardiac allograft recipient for being at-risk for developing cardiac allograft vasculopathy (CAV), Major Cardiac Events (MACE), and Graft Failure Due to CAV (GFDCAV), the method comprising the steps of:
measuring an amount of a first anti-phosphorylcholine natural antibody within at least one biological sample from a cardiac allograft recipient;
comparing the amount of the first anti-phosphorylcholine natural antibody in the biological sample with the amount of the first natural antibody in a control sample;
wherein a decrease in the amount of the first anti-phosphorylcholine natural antibody in the biological sample from the cardiac allograft recipient as compared to the amount of the first anti-phosphorylcholine natural antibody in the control sample indicates a diagnosis of the allograft recipient being either at-risk for or developing cardiac allograft vasculopathy (CAV), Major Cardiac Events (MACE), and Graft Failure Due to CAV (GFDCAV); and
administering a therapeutically effective amount of phosphorylcholine to the cardiac allograft recipient to treat and/or prevent cardiac allograft vasculopathy (CAV), which selectively enhances a natural antibody-mediated immune response, further comprising increasing levels of immunoglobulin M and/or immunoglobulin G anti-phosphorylcholine natural antibodies in the allograft recipient's serum, to reduce risk factors of Cardiac Allograft Vasculopathy (CAV), Major Cardiac Events (MACE), and Graft Failure Due to CAV (GFDCAV).

18. The method of claim 17, wherein the step of administering a therapeutically effective amount of phosphorylcholine further comprises reducing thrombosis and inflammation risks.

* * * * *